United States Patent
Sordella et al.

(10) Patent No.: US 8,323,883 B1
(45) Date of Patent: Dec. 4, 2012

(54) METHODS OF ASSESSING THERAPEUTIC BENEFITS OF PATIENTS HAVING CANCERS RESISTANT TO EPIDERMAL GROWTH FACTOR RECEPTOR KINASE INHIBITORS

(75) Inventors: Raffaella Sordella, Cold Spring Harbor, NY (US); Silvia Fenoglio, Bayville, NY (US); Trine Lindsted, Oyster Bay, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 18 days.

(21) Appl. No.: 12/903,133

(22) Filed: Oct. 12, 2010

Related U.S. Application Data

(60) Provisional application No. 61/250,291, filed on Oct. 9, 2009.

(51) Int. Cl.
*G01N 33/48* (2006.01)
*G01N 33/53* (2006.01)

(52) U.S. Cl. .......... 435/4; 435/6.1; 435/6.11; 435/6.14; 435/7.1; 435/7.23

(58) Field of Classification Search .................. None
See application file for complete search history.

(56) References Cited

U.S. PATENT DOCUMENTS

| | | |
|---|---|---|
| 2006/0211060 A1 | 9/2006 | Haley et al. |
| 2008/0066741 A1 | 3/2008 | LeMahieu et al. |
| 2008/0234264 A1 | 9/2008 | Bell et al. |
| 2008/0312260 A1 | 12/2008 | Haley et al. |
| 2009/0022726 A1 | 1/2009 | Zaki et al. |
| 2009/0238825 A1 | 9/2009 | Kovacevich et al. |
| 2009/0286850 A1 | 11/2009 | Shaaban et al. |
| 2009/0297436 A1 | 12/2009 | Garcia-Martinez et al. |
| 2009/0297513 A1 | 12/2009 | Garcia-Martinez et al. |
| 2010/0129357 A1 | 5/2010 | Garcia-Martinez et al. |
| 2010/0135983 A1 | 6/2010 | Hyde et al. |
| 2010/0137246 A1 | 6/2010 | Hyde et al. |
| 2010/0143294 A1 | 6/2010 | Smith |
| 2010/0150936 A1 | 6/2010 | Edvardsen et al. |

FOREIGN PATENT DOCUMENTS

| | | |
|---|---|---|
| WO | WO 2008/154927 A1 | 12/2008 |
| WO | WO 2010/065078 A1 | 6/2010 |

OTHER PUBLICATIONS

Finbloom et al., 1995, Cellular Signalling 7:739-745.*
Aaronson et al., 2002, Science 296:1653-1655.*
Trécul et al., 2012, Genes Nutr. 7:111-125.*
Catlett-Falcone et al., "Constitutive Activation of Stat3 Signaling Conferes Resistance to apoptosis in Human U266 Myeloma Cells," *Immunity* 10:105-115 (1999).
Colomiere et al., "Cross Talk of Signals Between EGFR and IL-6R Through JAK2/STAT3 Mediate Epithelial-Mesenchymal Transition in Ovarian Carcinomas," *British Journal of Cancer* 100:134-144 (2009).
Gao et al., "Mutations in the EGFR Kinase Domain Mediate STAT3 Activation Via Il-6 Production in Human Lung Adenocarcinomas," *The Journal of Clinical Investigation* 117:3846-3856 (2007).
Grivennikov and Karin, "Autocrine IL-6 Signaling: A Key Event in Tumorigenesis?," *Cancer Cells* 13:7-9 (2008).
Haura et al., "Activated Epidermal Growth Factor Receptor-Stat-3 Signaling Promotes Tumor Survival In Vivo in Non-Small Cell Lung Cancer," *Clinical Cancer Research* 11:8288-8294 (2005).
Ji et al., "Epidermal Growth Factor Receptor Variant III Mutations in Lung Tumorigenesis and Sensitivity to Tyrosine Kinase Inhibitors," *PNAS* 103:7817-7822 (2006).
Lee et al., "Epigenetic Modification of SOCS-1 Differentially Regulates STAT3 Activation in Response to Interleukin-6 Receptor and Epidermal Growth Factor Receptor Signaling Through JAk and/or MEK in Head and Neck Squamous Cell Carcinomas," *Mol. Cancer Ther*. 5(1):8-19 (2006).
Lynch et al., "Activating Mutations in the Epidermal Growth Factor Receptor Underlying Responsiveness of Non-Small-Cell Lung Cancer to Gefitinib," *The New England Journal of Medicine* 350(21):2129-2139 (2004).
Pao et al., "Acquired Resistance of Lung Adenocarcinomas to Gefitinib or Erlotinib is Associated with a Second Mutation in the EGFR Kinase Domain," PLOS Medicine 2:0225-0235 (2005).
Sansone et al., "IL-6 Triggers Malignant Features in Mammospheres from Human Ductal Breast Carcinoma and Normal Mammary Gland," *The Journal of Clinical Investigation* 117(12):3988-4002 (2007).
Schafer and Brugge, "IL-6 Involvement in Epithelial Cancers," *The Journal of Clinical Investigation* 117(12):3660-3663 (2007).
Trikha et al., "Targeted Anti-Interleukin-6 Monoclonal Antibody Therapy for Cancer: A Review of the Rationale and Clinical Evidence," *Clinical Cancer Research* 9:4653-4665 (2003).
Wang et al., "Current and Potential Inflammation Targeted Therapies in Head and Neck Cancer," *Elsevier* 9:389-395 (2009).

* cited by examiner

*Primary Examiner* — Elizabeth C Kemmerer
(74) *Attorney, Agent, or Firm* — Wolf, Greenfield & Sacks, P.C.

(57) ABSTRACT

Cancer treatment with a combination of an Epidermal Growth Factor Receptor tyrosine kinase inhibitor and an Interleukin-6 inhibitor.

7 Claims, 11 Drawing Sheets

| Target | Compound | Source | Phase |
|---|---|---|---|
| *Small molecule kinase inhibitors* | | | |
| Bcr-Abl, c-Kit, PDGF | Imatinib mesylate (Glivec®, Gleevec™) | Novartis | L-2001 |
| EGFR | Gefitinib (Iressa™) | AstraZeneca | L-2002 |
| EGFR | Erlotinib hydrochloride (Tarceva™) | Roche/Genentech/OSI | III |
| EGFR, ErbB2, ErbB3/4 | CI-1033 (irreversible inhibitor) | Pfizer | II |
| EGFR, ErbB2 | EKB-569 (irreversible inhibitor) | Wyeth-Ayerst | II |
| EGFR, ErbB2 | GW-2016 | GlaxoSmithKline | II |
| VEGFR | PTK-787/ZK-22584 | Novartis/Schering | II/III |
| VEGFR (EGFR) | ZD-6474 | AstraZeneca | II |
| PDGFR, VEGFR, FGFR | SU-6668 | Pharmacia/Sugen | I/II |
| VEGFR, PDGF, c-kit, Flt-3 | SU-11248 | Pharmacia/Sugen | I/II |
| VEGFR, FGFR | CP-547632 | Pfizer | I/II |
| VEGFR, FGFR, PDGFR (Flt-4) | CHR-200131 | Chiron | I |
| VEGFR, PDGFR, Flt-3 | CEP-7055 | Cephalon | I |
| VEGFR, PDGFR | AG-13736 | Pfizer/Agouron | I |
| VEGFR, c-Kit | KRN-633 | Kirin | I |
| Flt-3, PKC (PDGFR, c-kit) | PKC-412 | Novartis | II |
| Flt-3 | CT-53518 | Millennium | I |
| Flt-3 | CEP-701 | Cephalon | II |
| *Monoclonal antibodies* | | | |
| ErbB2 | Trastuzumab (Herceptin®) | Genentech | L-1998 |
| ErbB2 | MDX-210 | Medarex | I |
| ErbB2 | 2C4 | Genentech | I |
| EGFR | IMC-1C11 | ImClone Systems | I |
| EGFR | Cetuximab (Erbitux™) | ImClone Systems | III |
| EGFR | ABX-EGF | Abgenix | II |
| EGFR | EMD-72000 | Merck KgaA | I |
| EGFR | RH3 | York Medical | II |
| EGFR | MDX-447 | Medarex/Merck KgaA | I |
| ErbB2 | BsAB 2B-1 | Chiron | IB/II |
| VEGFR2 | HuMV833 | EORTC | I |
| PDGFβ | CDP-860 | Celltech | I/II |
| *Other approaches* | | | |
| ErbB2 | APC8024 (vaccine) | Dendreon | I |
| EGFR | DAB389EGF (hDT-hEGF fusion protein) | Seragen | II |
| VGFR1 mRNA | PRL4610 (nuclease-stabilized hairpin ribozyme) | Ribozyme Pharm | I/II |
| IGF 1R mRNA | INX-4437 (antisense oligonucleotide) | INEX | I |
| ErbB2 | 17-AAG (geldanamycin derivative inhibits Hsp90) | Kosan | I |

METHODS OF ASSESSING THERAPEUTIC BENEFITS OF PATIENTS HAVING CANCERS RESISTANT TO EPIDERMAL GROWTH FACTOR RECEPTOR KINASE INHIBITORS

RELATED APPLICATIONS

The present application claims the benefit of the filing date of U.S. Provisional Application No. 61/250,291, filed on Oct. 9, 2009, the teachings of which are incorporated herein by reference in their entirety.

GOVERNMENT FUNDING

Not Applicable

BACKGROUND OF THE INVENTION

Much excitement has been generated by the finding that a group of non-small cell lung carcinoma (NSCLC) patients harboring oncogenic somatic activating mutations within the epidermal growth factor receptor (EGFR) benefit greatly from treatment with EGFR inhibitors, such as erlotinib and gefitinib. However, there is considerable heterogeneity in the response of these NSCLC patients to EGFR inhibitor treatment, with overall responses varying from 5% to 90% and remissions ranging from three months to more than five years.

Despite considerable progress, lung cancer remains one of the leading causes of death worldwide; mortality rates from lung cancer exceed those of breast, prostate and colon cancer combined. New treatment methods are needed therefore.

SUMMARY OF THE INVENTION

It is shown herein that an interleukin-6 (IL-6) inhibitor, such as an anti-IL-6 antibody or an IL-6-targeting siRNA, unexpectedly re-sensitizes EGFR tyrosine kinase inhibitor-resistant cancer cells to an EGFR tyrosine kinase inhibitor, such as erlotinib or gefitinib.

Accordingly, one embodiment described herein relates to a method of treating an EGFR tyrosine kinase inhibitor-resistant cancer in a subject, e.g., suppressing further growth of the cancer or resulting in regression of the cancer. The method includes administering to a subject in need of the treatment a combination comprising an EGFR tyrosine kinase inhibitor (e.g., erlotinib or gefitinib) and an Interleukin-6 inhibitor (e.g., an anti-IL-6 antibody, an anti-IL-6 receptor antibody, or an a small inhibitory RNA (siRNA) that targets IL-6). Each of the EGFR tyrosine kinase inhibitor and the IL-6 inhibitor is administered in an amount that is therapeutically effective when the two are administered as a combination drug therapy, including, but are not limited to, inhibiting the growth of the EGFR tyrosine kinase inhibitor-resistant cancer, reducing tumor volume, enhancing apoptosis of EGFR tyrosine kinase inhibitor resistant cancer cells, increasing the number of apoptotic cancer cells in the subject, and/or increasing sensitivity of EGFR tyrosine kinase inhibitor resistant cancer cells to the EGFR tyrokine kinase inhibitor.

Other embodiments relate to a method of increasing the sensitivity of EGFR tyrosine kinase inhibitor-resistant cancer cells to an EGFR tyrosine kinase inhibitor, a method of reducing resistance of EGFR tyrosine kinase inhibitor-resistant cancer cells to an EGFR tyrosine kinase inhibitor in a subject, a method of increasing the number of apoptotic cancer cells in a subject, and a method of enhancing apoptosis of EGFR tyrosine kinase inhibitor-resistant cancer cells in a subject. These methods each include administering to a subject in need thereof a combination comprising an EGFR tyrosine kinase inhibitor (e.g., erlotinib or gefitinib) and an IL-6 inhibitor (e.g., an anti-IL-6 antibody, an anti-IL-6 receptor antibody, or an antisense oligonucleotide targeting IL-6, such as a small inhibitory RNA (siRNA).

In any of the above-described methods, the subject in need thereof can be an individual who has EGFR tyrosine kinase inhibitor-resistant cancer, such as an individual (e.g., a NSCLC patient) carrying an oncogenic mutation associated with resistance to an EGFR tyrosine kinase inhibitor, including, but are not limited to, the variant III mutation, a KRAS mutation, a combination of L858R and a second mutation in the EGFR (e.g., T790M), or a combination of delE746-A750 and a second mutation in the EGFR (e.g., T790M). The EGFR tyrosine kinase inhibitor and the IL-6 inhibitor can be administered simultaneously or sequentially, provided that they are administered sufficiently closely in time that they produce the desired outcome. In specific embodiments, the IL-6 inhibitor is administered in a dose sufficient to increase sensitivity of EGFR tyrosine kinase inhibitor-resistant cancer cells to the EGFR tyrosine kinase inhibitor, reduce resistance of the EGFR tyrosine kinase inhibitor-resistant cancer cells to the EGFR tyrosine kinase inhibitor, and/or induce apoptosis of EGFR tyrosine kinase inhibitor-resistance cancer cells in the subject.

Also within the scope of this disclosure are (i) a pharmaceutical composition for use in treating a EGFR tyrosine kinase inhibitor-resistant cancer, increasing the sensitivity of EGFR tyrosine kinase inhibitor-resistant cancer cells to an EGFR tyrosine kinase inhibitor, enhancing apoptosis of EGFR tyrosine kinase inhibitor-resistant cancer cells, or increasing the number of apoptotic cancer cells in a subject, the pharmaceutical composition containing (comprising) an EGFR tyrosine kinase inhibitor and an IL-6 inhibitor and, optionally, further comprising one or more additional anti-cancer compounds; (ii) a kit containing the pharmaceutical composition and, optionally, a pharmaceutically acceptable carrier, and (iii) use of the pharmaceutical composition in manufacturing a medicament for use in treating a EGFR tyrosine kinase inhibitor-resistant cancer, increasing the sensitivity of EGFR tyrosine kinase inhibitor-resistant cancer cells to an EGFR tyrosine kinase inhibitor, enhancing apoptosis of EGFR tyrosine kinase inhibitor-resistant cancer cells, or increasing the number of apoptotic cancer cells.

Another embodiment of this invention relates to a method of assessing the likelihood that a subject with EGFR tyrosine kinase inhibitor-resistant cancer (e.g., EGFR tyrosine kinase inhibitor-resistant NSCLC) would benefit from therapy that increases sensitivity to an EGFR tyrosine kinase inhibitor such as erlotinib. This method includes (a) obtaining a cellular tissue sample from the subject, the sample comprising cancer cells resistant to an EGFR tyrosine kinase inhibitor (e.g., cells carrying one or more of the oncogenic mutations in the EGFR that are associated with EGFR tyrosine kinase inhibitor resistance), (b) determining the presence or absence of an oncogenic mutation in the EGFR of the cancer cells; and (c) determining at least one of the following levels in the sample: Il-6 mRNA level, IL-6 protein level, STAT3 phosphorylation level, and JAK activity level. If the cancer cells carry the oncogenic mutation in the EGFR and the at least one level determined in (c) is elevated, the subject has a greater likelihood of benefiting from the therapy than a subject who does not carry the onogenic mutation and shows a normal level of Il-6 mRNA, IL-6 protein, STAT3 phosphorylation, and/or JAK activity.

Also described herein is a method of suppressing the growth of a cell carrying an oncogenic mutation in the EGFR that is associated with resistance to an EGFR tyrosine kinase inhibitor, the method comprising contacting the cell with an EGFR tyrosine kinase inhibitor (e.g., erlotinib or gefitinib) and an IL-6 inhibitor (e.g., an anti-IL-6 antibody or an anti-IL-6 receptor antibody) to suppress the growth of the cell. The cell to be treated in this method can be a cancer cell, such as a lung cancer cell (e.g., a NSCLC cell). In some embodiments, the cell is in a subject.

Yet another embodiment is a method of increasing the number of apoptotic cells in a population of cells containing EGFR tyrosine kinase inhibitor-resistant cancer cells, which can carry an oncogenic mutation in the EGFR such as L858R or delE746-A750. This method includes contacting the population of cells with an EGFR kinase inhibitor and an IL-6 inhibitor, such as those mentioned herein, to increase the number of apoptotic cells in the population of cells. The population of cells, which may contain both cancer cells and non cancer cells, can be in a subject.

BRIEF DESCRIPTION OF THE DRAWINGS

The figures are illustrative only and are not required for enablement of the invention disclosed herein.

FIG. 6 shows an overview of tyrosine kinase inhibitors, including inhibitors against EGFR.

DETAILED DESCRIPTION OF THE INVENTION

Figure 1:
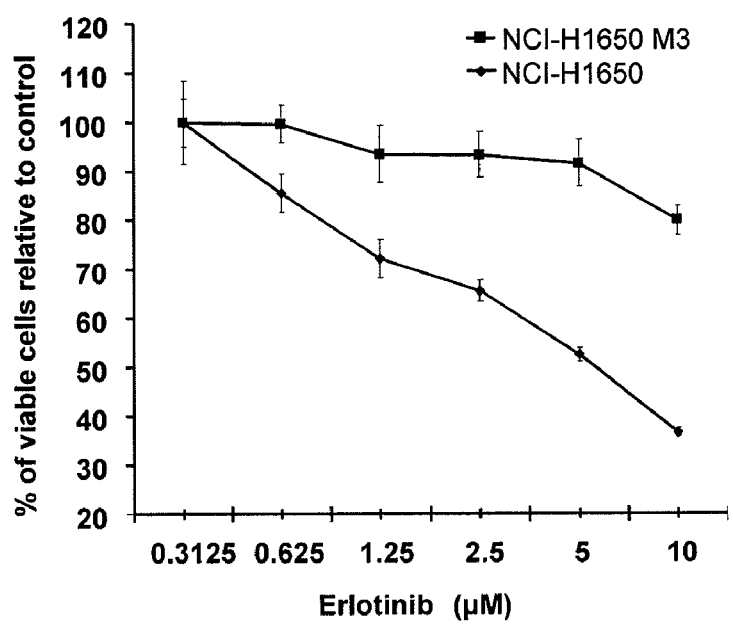
FIG. 1 is a diagram showing that the NCI-H1650 M3 cells displayed a decreased sensitivity to erlotinib due to a decrease in apoptotic response. Panel A: a chart showing the percentages of viable NCI-H1650 and NCI-H1650 M3 cells in the presence of erlotinib at various concentrations 72 hours after erlotinib treatment. Panel B: a photo showing decreased apoptosis (indicated by the levels of CL-PARP) in erlotinib-resistant NCI-H1650 M3 cells treated with erlotinib.
Figure 1:
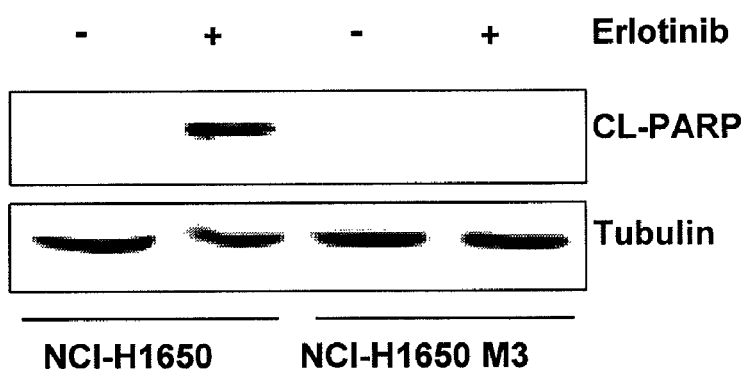

Described herein is a method of treating a cancer in a subject, including administering to a subject in need of the treatment an effective amount of an EGFR inhibitor (e.g., an EGFR tyrosine kinase inhibitor) and an effective amount of an IL-6 inhibitor. In some embodiments, an effective amount(s) of the EGFR tyrosine inhibitor and/or the IL-6 inhibitor such that co-administration of the two inhibitors leads to an anti-cancer effect, including, but are not limited to, enhancement of cancer cell apoptosis, suppression of cancer growth, and regression of tumor volume. In one example, the amount of the IL-6 inhibitor is sufficient to increase sensitivity of EGFR tyrosine kinase inhibitor-resistant cancer cells to the EGFR tyrosine kinase inhibitor, and/or reduce resistance of the EGFR tyrosine kinase inhibitor—resistant cancer cells to the EGFR tyrosine kinase inhibitor.

A "subject", as used herein, refers to a vertebrate mammal, including, but not limited to, human, mouse, rat, dog, cat, horse, cow, pig, sheep, goat, or non-human primate. In some embodiments, the subject is a human. The terms "subject," "patient" and "individual" are used interchangeably.

A "subject in need of treatment", as used herein, means a subject who is identified as being in need of treatment. For instance, a subject in need of cancer treatment is a subject identified as having cancer, at risk for developing cancer, or suspected of having cancer. A subject may be diagnosed as being in need of treatment by a healthcare professional and/or by performing one or more diagnostic assays. A subject in need of cancer treatment may be a subject diagnosed with cancer or being at risk of cancer by a healthcare professional. Diagnostic assays to evaluate if a subject has a cancer or is at risk for developing cancer are known in the art.

In one example, the subject in need of the treatment is a human patient carrying a cancer that is resistant to an EGFR tyrosine kinase inhibitor (e.g., lung cancer such as NSCLC). Such subjects can be identified by their responsiveness to an EGFR tyrosine kinase inhibitor treatment. Alternatively, they can be identified by examining whether their cancer cells carry particular oncogenic mutations in the EGFR. It is known in the art that certain mutations in the EGFR, for example, the variant III mutation, a KRAS mutation, a combination of L858R and a second mutation in the EGFR (e.g., T790M), or a combination of delE746-A750 and a second mutation in the EGFR (e.g., T790M), are associated with resistance to EGFR tyrosine kinase inhibitor. See, e.g., Ji et al., PNAS 103 (20): 7817-7822, 2006; Pao et al., PLoS Medicine 2:e17, 2005; and Pao et al., PLos Medicine 2(2):e73, 2005. Thus, cancer cells carrying one or more of these mutations would be resistant to an EGFR tyrosine kinase inhibitor, such as erlonitib or gefitinib.

As used herein, "treating a cancer" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect the cancer, the symptoms of the cancer, or the predisposition toward the cancer. Treating cancer includes, but is not limited to, reducing risk for developing a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis or increasing the amount of apoptotic cancer cells.

Cancers to be treated in the method described herein can be lung cancer (e.g., NSCLC), a cancer associated with an EGFR mutation (e.g., the T790M mutation), a cancer associated with upregulated cMET signaling, or a cancer that is resistant to an EGFR tyrosine kinase inhibitor such as erlotinib or gefinitib.

Oncogenic mutations in cellular receptors can lead to increased intracellular signaling. Oncogenic mutations include mutations that allow the receptor to induce signaling in the absence of ligand stimulation and mutations that lead to increased intracellular signaling once a receptor is activated by a ligand. In addition, oncogenic mutations can induce over-expression of cellular receptors, which results in an increase in intracellular signaling because additional cellular receptors are available. The increased intracellular signaling can subsequently result in an increased growth rate of a cell and uncontrolled proliferation. A number of cancer cells are characterized by increased receptor activation. In addition, cancer cells with increased receptor activation often become dependent on these signaling pathways. If the signaling pathway on which the cancer cell has become dependent is inhibited or suppressed, the ability of the cancer cell to survive is compromised and, in many instances, the cancer cells can no longer survive. The dependency of cancer cells on a specific signaling pathway therefore offers a therapeutic window for anti-cancer therapy; regular (non-cancer) cells have not acquired this dependency on specific receptor signaling and, in contrast to cancer cells, can survive when challenged with an inhibitor or suppressor for such a pathway.

An example of a cellular receptor that can acquire oncogenic activating mutations and/or is overexpressed in cancer cells is the Epidermal Growth Factor Receptor (EGFR). EGFR (also referred to as ErbB-1 or HER1) is a member of the ErbB family of receptor tyrosine kinases, which also includes ErbB2 (Her2), ErbB3 (HER3) and ErbB4 (Her4). Examples of activating oncogenic mutations in EGFR include a deletion at exon 19 and a leucine to arginine (L858R) missense substitution. These activating mutations lead to increased EGFR mediated intracellular signaling. In addition, overexpression of the EGFR receptor can also result in increased intracellular signaling. Overexpression of EGFR has been observed in a number of cancers, including human breast tumors, and can be caused by the amplification of the EGFR gene. Methods for suppressing EGFR signaling include the administration of anti-EGFR antibodies and the administration of small molecules that can act as inhibitors of the tyrosine kinase domain of the EGFR receptor.

The term inhibition, as used herein, includes both complete inhibition and partial inhibition. Thus, inhibitors, as used herein, include compounds and agents that can completely inhibit a pathway or interaction, or partially inhibit a pathway or interaction.

EGFR inhibitors, as used herein, include any compound or agent that can bind to any protein (including receptors) in the EGFR signaling pathway and thereby suppress the EGFR signaling activity. Non-limiting examples of EGFR inhibitors are antibodies that bind the EGFR receptor, antibodies that bind other receptors in the EGFR family and small molecules that can suppress EGFR signaling (such as EGFR tyrosine kinase inhibitors). An overview of selected EGFR inhibitors and inhibitors against related pathways is provided in FIG. 6.

Antibodies that bind EGFR and thereby suppress EGFR signaling are known in the art, including cetuximab (Erbitux) and panitumumab (Vectibix). Trastuzumab (Herceptin) is an antibody that can suppress EGFR signaling by binding ErbB2. Binding of the antibody to ErbB2 blocks the dimerization of ErbB2 and EGFR thereby preventing initiation of the EGFR signaling pathway. Use of any antibody that can bind EGFR or another receptor that can dimerize with EGFR to neutralize EGFR signaling is within the scope of this disclosure.

EGFR tyrosine kinase inhibitors bind the ATP binding pocket of the EGFR receptor and prevent ATP from binding. As a result binding of the inhibitor results in the suppression of EGFR mediated intracellular signaling. EGFR tyrosine kinase inhibitors include both reversible and irreversible inhibitors. Most reversible inhibitors are based on quinazolines and include gefitinib (Iressa; N-(3-Chloro-4-fluorophenyl)-7-methoxy-6-(3-morpholin-4-ylpropoxy)quinazolin-4-amine), erlotinib (Tarceva; N-(3-ethynylphenyl)-6,7-bis(2-methoxyethoxy)quinazolin-4-amine) and lapatinib (Tykerb, GW572016; N-[3-chloro-4-[(3-fluorophenyl)methoxy]phenyl]-6-[5-[(2-methylsulfonylethylamino)methyl]-2-furyl]quinazolin-4-amine). Irreversible inhibitors permanently modify the tyrosine kinase domain of EGFR, thereby suppressing EGFR signaling. Irreversible inhibitors include CI-1033, EKB-569 and HKI-272 (See e.g., Zhang et al., 2007, JCI 117: 2051-2058). The binding of a EGFR-TKI to EGFR leads to the induction of apoptosis of the cell expressing the EGFR, thereby providing a method for cancer treatment. It should be appreciated that the terms EGFR tyrosine kinase inhibitor and EGFR kinase inhibitor are used interchangeably herein.

Cancers that are dependent on a specific intracellular signaling pathway and that are being challenged by inhibitors against that pathway, such as antibodies or small-molecule inhibitors, may become resistant to this challenge. The cancer can become resistant to the challenge, for instance, by developing alternative signaling pathways or by upregulating existing pathways to allow the cancer cell to proliferate in the presence of the inhibitor.

Cancers that are dependent on EGFR signaling initially respond to treatment by EGFR inhibitors, but later can become resistant to such treatment. For instance, cancers with increased EGFR signaling that are challenged with one or more EGFR-TKIs can initially show a strong response but can develop additional mutations in EGFR to "work around the inhibitor" or upregulate alternative signaling pathways to compensate for the suppression in EGFR signaling. Cancers that are no longer responsive to EGFR-TKIs have been shown to have acquired the EGFR mutation T790M or to have upregulated the c-Met signaling pathway (See e.g., Zhang et al., 2007, JCI 117: 2051-2058).

It is shown herein that, unexpectedly, cancer cells with oncogenic EGFR mutations that have become resistant to treatment with an EGFR tyrosine kinase inhibitor are responsive to treatment by the combination of an EGFR tyrosine kinase inhibitor and an IL-6 inhibitor. Until the work described herein, the only known responses of cells to treatment by EGFR tyrosine kinase inhibitors was the development of an oncogenic T790M mutation and upregulation of the c-Met signaling pathway. Neither the acquisition of the oncogenic T790M mutation nor the upregulation of cMet would imply that EGFR tyrosine kinase inhibitor-resistant cells can be treated by a combination of EGFR tyrosine kinase inhibitors (to which the cells has become resistant) and an IL-6 inhibitor. Thus, in one aspect, the invention provides methods for re-sensitizing and/or reducing the sensitivity of EGFR— tyrosine kinase inhibitor-resistant cancer cells to EGFR— tyrosine kinase inhibitors.

Also described herein are treatment methods for cancers in which cells exhibit increased EGFR signaling and/or cells have become dependent on EGFR signaling. Cancers that have cells with increased EGFR signaling and/or cells that have become dependent on EGFR signaling include breast cancer, pancreatic cancer and lung cancer. Cancers that have increased EGFR signaling can readily be identified by standard biochemical assays, for instance by determining the presence of phosphorylated signaling proteins or by the detecting the presence of increased mRNA levels of proteins involved in the EGFR intracellular signaling. In some embodiments, the cancer treated according to the methods of the invention has an Epidermal Growth Factor Receptor that has acquired an oncogenic mutation. In some embodiments, the oncogenic mutation is L858R or delE746-A750. In some embodiments, the cancer is Non Small Cell Lung Carcinoma.

In some embodiments, the present invention relates to methods of modulating a cancer treatment regimen by providing a cancer patient one or more EGFR inhibitors and/or one or more IL-6 inhibitors and modulating the treatment regimen, if such a patient is not responsive to treatment. The patient can carry an EGFR with an oncogenic mutation.

Interleukin-6 (IL-6) was originally characterized as a regulator of immune and inflammatory responses and IL-6 can be secreted by macrophages in response to the presence of pathogens. IL-6 can interact with the IL-6 receptor (IL-6R) leading to the activation of the JAK family of kinases, which can stimulate a variety of signaling pathways. IL-6 has been implicated in a variety of cancers, including leukemia, lymphoma, lung cancer, prostate cancer and cancers associated with inflammation (See e.g., Trikha et al. Clin Cancer Res 2003, 9: 4653), and increased levels of IL-6 have been found in multiple epithelial tumors (See e.g., Schafer et al. J Clin Inv., 2007, 117: 3660). It is shown herein that the suppression of IL-6 signaling can restore the sensitivity of EGFR-TKI resistant cells to EGFR-TKIs. The invention embraces the suppression of IL-6 signaling by any method. For instance, IL-6 signaling can be suppressed by limiting the availability of IL-6 or by suppressing the activity of the IL-6 receptor. In some embodiments, the availability of IL-6 is reduced by the administration of an IL-6 inhibitor. In some embodiments, the availability of IL-6 is reduced by the administration of an antibody against IL-6. In some embodiments, the availability of the IL-6 receptor is limited by the administration of an anti-IL6 receptor antibody.

There are a number of methods available for reducing the availability of IL-6 and IL6- receptors in order to suppress IL-6 initiated signaling, thereby restoring the sensitivity of EGFR tyrosine kinase inhibitor-resistant cells to EGFR tyrosine kinase inhibitors. For example, IL-6 signaling can be suppressed by reducing the inflammation and/or the immune response in a subject, e.g., in tissue near or in contact with the cancer, or by administering anti-inflammatories and/or immunosuppressants.

In another example, IL6 signaling is suppressed by the administration of an IL-6 inhibitor, which can be an antibody against IL-6, an antibody against an IL-6 receptor, or a an antisense oligonucleotide targeting IL-6 (e.g., siRNA). Antibodies against IL-6 are known in the art and include BE-8 and CNT0328 (See e.g., Trikha et al., Clin Cancer Res 2003, 9: 4653 or US20090022726). Antibodies against IL-6R are known in the art and include PM1 (Hirata et al., J Immunol 143, 2900, 1986), AUK12-20, AUK64-7, AUK146-15 (WO92/19759), MRA (U.S. Pat. No. 5,888,510), AB-227-NA and Tocilizumab (See e.g., Hashizume, Rheumat Int 2009, Jul. 29, epub). These antibodies are capable of neutralizing IL-6 signaling via binding to either IL-6 or its receptor. Such antibodies can also be prepared via routine technologies.

As used herein, the term "antibody" refers to naturally-occurring antibodies, antigen-binding fragments thereof, such as $F(ab')_2$ and Fab, and recombinant antibodies, such as chimeric antibody, humanized antibody, single-chain antibody, and domain antibody. A naturally-occurring antibody can be obtained from any suitable species, such as human, rabbit, mouse, guinea pig, and rat, and can be of any immunoglobulin class including IgG, IgM, IgE, IgA, IgD, and any subclass thereof.

Any of these antibodies can be prepared via routine techniques, e.g., hybridoma technology or recombinant technology. See, e.g., Kohler et al. *Nature* 256:495; 1975; Kosbor et al. *Immunol Today* 4:72, 1983; Cole et al. *Proc. Natl. Acad. Sci. USA* 80:2026, 1983; Cole et al. Monoclonal Antibodies and Cancer Therapy, Alan R. Liss, Inc., pp. 77-96, 1983; Green et al., *Nature Genetics* 7:13, 1994, Morrison et al. *Proc. Natl. Acad. Sci. USA* 81:6851, 1984; Neuberger et al. *Nature* 312:604, 1984; and Takeda et al. *Nature* 314:452, 1984; and U.S. Pat. Nos. 4,376,110, 5,545,806, and 5,569,825, 4,946, 778, and 4,704,692.

An antisense oligonucleotide specific to a target protein (e.g., IL-6) is an oligonucleotide (DNA or RNA) at least a portion of which is complementary (i.e., completely or partially) to a fragment of the nucleic acid coding for the target protein (either the sense chain or the antisense chain), i.e., capable of forming a double-strand duplex via base-pairing according to the standard Watson-Crick complementarity rules. In one example, it is an interfering RNA (e.g., a small inhibitory RNA or siRNA) that blocks expression of the target protein via RNA interference. When necessary, the antisense oligonucleotide to be used in the methods described herein can be modified, e.g., containing a modified nucleoside that includes a modified heterocyclic base, a modified sugar moiety, or any combination thereof, or a non-phosphodiester linkage between two of its nucleotides.

In the methods described herein, an IL-6 inhibitor can be administered in combination with an anti-inflammatory and/or an immunosuppressant. Additional inhibitors of IL-6 signaling that can be co-used, including, but are not limited to, dominant-negative IL-6 mutants (i.e., mutants capable of binding to an IL-6 receptor but do not activate the receptor) and small molecules that can prevent the interaction between IL6 and its receptor. Additional IL-6 signaling suppressors that can be used are agents, including polypeptides and antibodies, that can prevent downstream IL-6 signaling. These agents include STAT3 and JAK inhibitors.

It is shown herein that contacting a cell with a combination of an EGFR tyrosine kinage inhibitor and an IL-6 inhibitor can induce cell apoptosis. Thus, this combination can be used to inducing apoptosis in a cell, which may be resistant to an EGFR tyrosine kinase inhibitor.

It is also shown herein that contacting a population of cells with a combination of an EGFR tyrosine kinase and an IL-6 inhibitor can increase the number of apoptotic cells in that population of cells. Accordingly, some embodiments feature a method of increasing the number of apoptotic cells in a population of cells, including contacting the population of cells with a combination of an EGFR tyrosine kinase inhibitor and an Interleukin-6 inhibitor at an amount sufficient to increase the number of apoptotic cells in a population of cells. The contact step can be performed by administering the combination to a subject in need.

As shown herein, cells that have become resistant to an EGFR tyrosine kinase inhibitor have a decreased ability to undergo apoptosis. Contacting these resistant cells with a combination of an EGFR tyrosine kinase inhibitor and an IL-6 inhibitor re-sensitizes these cells to the EGFR tyrosine kinase inhibitor, thereby allowing these cells to undergo apoptosis.

It is shown herein that contacting a cell with a combination of an EGFR tyrosine kinase inhibitor and an IL6 inhibitor can suppress the growth of a cell. Thus, one embodiment of the invention relates to a method of suppressing the growth of a cell, which can be a cancer cell. This method includes contacting the cell with an EGFR kinase inhibitor and an IL-6 inhibitor to suppress the growth of the cell. In some embodiments, the cell is in a subject. In some embodiments, the cell is a cancer cell. Thus, the invention provides methods for treating a cancer in a subject by contacting a cell in a subject with an EGFR-TKI and an IL-6 inhibitor. In some embodiments, the cancer cell is a lung cell. In some embodiments, the cancer cell is a non-small cell lung carcinoma (NSCLC) cell. In some embodiments, the cell comprises an oncogenic mutation in the EGFR.

Also described herein is a method of treating cancer in a subject by contacting a population of cells in the subject with the combination of a therapeutically effective amount of EGFR tyrosine kinase inhibitor and a therapeutically effective amount of an IL-6 inhibitor, resulting in an increase in the percentage of apoptotic cells in the subject. In some embodiments, the cancer cell is a lung cell. In some embodiments, the cancer cell is a non-small cell lung carcinoma (NSCLC) cell. In some embodiments, the one or more cells in the population of cells have an oncogenic mutation in the EGFR.

A cell that has become resistant to an EGFR-tyro sine kinase inhibitor likely has acquired certain characteristics (e.g., mutations) that render the cell resistant to the inhibitor. For instance, the cell can acquire an additional mutation in the EGFR, or the cell can acquire increased cMet signaling. The cell can also be characterized by having additional signaling pathway characteristics, such as increased STAT3 or JAK levels, compared to the levels of corresponding EGFR-TKI sensitive cells. In addition, the EGFR-TKI resistant cell can be characterized by increased IL-6 both at the mRNA and at the protein level when compared to the EGFR-TKI sensitive cell. If an EGRF-TKI resistant cell is determined to have any of these characteristics, the cell is a good candidate for resensitizing the cell to EGFR-TKI therapy (i.e., rendering the cell responsive again to contacting/treatment by an EGFR-TKI), through the administration of the combination of an EGFR-TKI and an IL6 inhibitor. Thus, in one aspect, the invention provides a method of assessing the likelihood that a subject with Epidermal Growth Factor Receptor kinase inhibitor-resistant cancer will benefit from therapy that increases sensitivity to a Epidermal Growth Factor Receptor kinase inhibitor, the method comprising (a) obtaining a cellular tissue sample from the subject; wherein the sample comprises non-small cell lung carcinoma (b) determining the presence or absence of an oncogenic mutation in the Epidermal Growth Factor Receptor of the cells from the sample; and (c) determining at least one of the following levels: Il-6 mRNA expression level, IL-6 level, STAT3 phosphorylation level, and JAK activity level, wherein if the oncogenic mutation in the Epidermal Growth Factor Receptor is present and the at least one level determined in (c) is elevated (relative to a control), the likelihood that the subject will benefit from the therapy is greater than if the oncogenic mutation in the Epidermal Growth Factor Receptor is not present and the at least one level determined in (c) is not elevated. In some embodiments, the cancer is non-small cell lung carcinoma (NSCLC). In some embodiments, the Epidermal Growth Factor Receptor kinase inhibitor is erlotinib. It should be appreciated that the sample is not limited to a cellular tissue sample and that the invention embraces obtaining any cell sample, in which the presence or absence of an oncogenic mutation in the Epidermal Growth Factor Receptor can be determined.

Also described herein are methods for establishing cell lines that are resistant to EGFR tyrosine kinase inhibitors. Cells that are resistant to an EGFR tyrosine kinase inhibitor can grow in the presence of increased concentrations of EGFR tyrosine kinase inhibitor. The cells described herein can be used a model cell system to evaluate potential cancer therapies and treatment options that are based on the administration of EGFR tyrosine kinase inhibitors. For instance, the cells can be evaluated for the presence of specific mutations and/or other characteristics that allow the cells to survive the increased concentration of EGFR tyrosine kinase inhibitor. In addition, potential new treatment methods (e.g., the co-administration of an EGFR tyrosine kinase inhibitor and a second agent) can be evaluated, using such cell lines, for their efficacy in suppressing the growth of the EGFR tyrosine kinase inhibitor resistant cell. Thus, in one aspect, described herein is an in vitro cell-based system, comprising an isolated human cell that is resistant to increased concentrations of an EGFR tyrosine kinase inhibitor.

The cell lines described above can be prepared by culturing parental cells (e.g., human cells) in the presence of an increased concentration of an EGFR tyrosine kinase inhibitor and isolate those that show resistance to the inhibitor. In some embodiments, the EGFR tyrosine kinase inhibitor resistant cell can grow in a concentration of EGFR tyrosine kinase inhibitor that is 2× or more, 5× or more, 10× or more, 20× or more, 50× or more, 100× or more, 1000× or more, or 10,000× or more than the IC50 of the EGFR tyrosine kinase inhibitor sensitive cell from which the EGFR tyrosine kinase inhibitor resistant cell is derived. In some embodiments, the EGFR tyrosine kinase inhibitor resistant cell can grow in the presence of 1 µM or more, 5 µM or more, 10 µM or more, 15 µM or more, 20 µM or more, 25 µM or more, 30 µM or more, 35 µM or more, 40 µM or more, 45 µM or more, or 50 µM or more erlotinib. In some embodiments, the EGFR tyrosine kinase inhibitor resistant cell is a lung cell. In some embodiments, the EGFR tyrosine kinase inhibitor resistant cell is a Non Small Cell Lung Carcinoma cell. In some embodiments, the oncogenic mutation is L858R or delE746-A750. In some embodiments, the EGFR tyrosine kinase inhibitor resistant cell is derived from a H1650 cell line. In some embodiments, the EGFR tyrosine kinase inhibitor resistant cell does not comprise a T790M mutation in the EGFR. In some embodiments, the EGFR-TKI resistant cell does not have increased cMET signaling when compared to the EGFR-TKI sensitive cell from which the EGFR tyrosine kinase inhibitor resistant cell was derived. In some embodiments, the cell further comprises at least one of the following characteristics: a substantial decrease in the ability to undergo apoptosis; a substantial decrease in cleavage of poly (ADP-ribose) polymerase (PARP); a substantial decrease of EGFR phosphorylation; STAT3 activation in an EGFR-independent manner; increased mRNA encoding interleukin-6 levels or increased interleukin-6 levels.

It should be appreciated that the disclosure herein also embraces the administration of, or the contacting of cells with, multiple EGFR inhibitors and IL-6 inhibitors. For instance, the invention embraces methods of treatments with a combination drug therapy comprising the administration of one EGFR inhibitor and one IL-6 inhibitor, the administration of multiple EGFR inhibitors and one IL-6 inhibitor, the administration of one EGFR inhibitor and multiple IL-6 inhibitors, and the administration of multiple EGFR inhibitors and multiple IL-6 inhibitors. Analogously, it should further be appreciated that all the methods, kits and pharmaceutical compositions disclosed herein, comprise combinations of one or more EGFR inhibitors with one or more IL6-inhibitors.

In any of the methods described herein, if applicable, the EGFR inhibitor and IL-6 inhibitor are administered in therapeutically effective amounts. In some embodiments, the EGFR inhibitor(s) and IL-6 inhibitor(s) are each administered in an amount that is therapeutically effective when the EGFR inhibitor(s) and IL-6 inhibitor(s) are administered as a combination drug therapy. An effective amount is a dosage of the inhibitors sufficient to provide a medically desirable result. An effective amount means that amount necessary to delay the onset of, inhibit the progression of, or halt the onset or progression of the particular condition or disease being treated. In the treatment of cancer an effective amount will be, for example, that amount necessary to inhibit cancer cell replication, suppress the further growth of the cancer, increase apoptosis in cancer cells, regress the cancer, reduce cancer cell load, or reduce one or more signs or symptoms of the cancer. Effective amount and therapeutically effective amount are used interchangeably herein.

Determining the therapeutically effective amounts of the EGFR inhibitors and IL-6 inhibitors described herein will be routine to the physician. In addition, a physician can find guidance on therapeutically effective amounts, toxicity and potential side effects of the administration of EGFR inhibitors and IL-6 inhibitors in the following references: Piccart-Gebhart et al., NEJM 353: 1659, 2005; Pirker et al., Lancet 2009, 373: 1525; Tomizawa et al., Lung Cancer 2009 Aug. 4, epub; Katayma et al., J Thorac Oncol 2009, Aug 18. epub; Hashizume, Rheumat Int 2009, Jul. 29, epub; Straub et al., Arthritis & Rheumatism, 54, 1778-1785, 2006; Mok et al., J Clin Oncology epub Sep. 8, 2009 10.2000/JCO.2008.21.5541. Furthermore, guidance for determining therapeutically effective doses can be found in the data disclosed by European and US regulatory agencies. For instance, the assessment reports for erlotinib (Tarceva, H—C-618) disclosed by the European Medicines Agency at emea.europa.eu/humandocs/Humans/EPAR/tarceva/tarceva.htm; the assessments reports for gefitinib (Iressa) disclosed by the European Medicines Agency at emea.europa.eu/humandocs/Humans/EPAR/iressa/iressa.htm (e.g., Doc.Ref.:EMEA/CHMP/563746/2008); the assessment reports for RoActerma (tocilizumab) disclosed by the European Medicines Agency at emea.europa.eu/humandocs/Humans/EPAR/RoActemra/RoActemra.htm (e.g., Doc. Ref. EMEA/26276/2099); and clinical trial studies on CNTO 328 published by the NIH (identifier NCT00841191). It will be routine to a physician to adjust the effective amounts of single drug therapy for the combination treatments disclosed herein. For instance, in assessing the particular amounts of the inhibitors for a combination therapy for a particular cancer a physician may start with the administration of amounts of the EGFR inhibitor and IL-6 inhibitor that are lower than the amounts used for single therapy, to test for any unwanted side effects of the combination therapy.

When administered to a subject, effective amounts will depend, of course, on the particular cancer being treated; the genotype of the specific cancer (e.g., does the cancer have a mutation in the EGFR receptor); the severity of the cancer; individual patient parameters including age, physical condition, size and weight, concurrent treatment, frequency of treatment, and the mode of administration. These factors are well known to the physician and can be addressed with no more than routine experimentation. In some embodiments, it is preferred to use the highest safe dose according to sound medical judgment.

The EGFR inhibitor(s) and IL-6 inhibitor(s) used in the combination therapies described herein may be administered simultaneously or sequentially. When the EGFR inhibitors and IL-6 inhibitors, as used in the combination therapies, are administered simultaneously they can be administered in the same or separate formulations, but are administered at the same time. In some embodiments, the EGFR inhibitor(s) and IL-6 inhibitors(s) used in the combination therapy disclosed herein are combined in one pharmaceutical composition. The administration of the EGFR inhibitor(s) and IL-6 inhibitor(s) through different delivery methods is also contemplated. For instance, an EGR inhibitor may be administered in a composition for oral delivery and an IL-6 inhibitor may be administered intravenously. The administration of the EGFR inhibitor(s) and IL-6 inhibitor(s) may also be temporally separated, meaning that each of the inhibitors is administered at a different time, either before or after, the administration of the other inhibitor. For instance, an EGFR inhibitor (e.g., EGFR tyrosine kinase inhibitor), may be administered prior to the administration of an IL-6 inhibitor (e.g., an IL-6R antibody). The separation in time between the administration of these inhibitors may be a matter of minutes or it may be longer, provided they are sufficiently close in time to have the desired effect (e.g., the treatment of the cancer). Additional therapeutic agents (e.g., an anti-inflammatory) may be administered prior to the administration of the EGFR inhibitors and IL-6 inhibitors, after the administration of the EGFR inhibitors and IL-6 inhibitors or interspersed between the administration of the EGFR inhibitors and IL-6 inhibitors Additional administration regimes are also contemplated. For instance, a subject may receive a constant dose of one or more anti-inflammatories or immunosuppressants in conjunction with the administration of the EGFR inhibitors and IL-6 inhibitors. It should be appreciated that, analogously to their use in the methods of administration described above, the EGFR inhibitors and IL-6 inhibitors used in the methods comprising contacting a cell or contacting a population of cells, may be used by contacting the cell or population of cells simultaneously or sequentially.

Methods for increasing apoptosis in cancer cells are also provided herein. Such methods can be performed by contacting a population of cells that contain cancer cells with an EGFR inhibitor and an IL-6 inhibitor. In some embodiments, the amounts of the inhibitors are sufficient to increase the number of apoptotic cells in the population by at least 10%, 20%, 30%, 40%, 50%, 60%, 70%, 80%, 90% or 100%. In other embodiments, the number of apoptotic cells in a population of cells is increased by at least two-fold, three-fold, four-fold, or five-fold. In some embodiments, the number of apoptotic cells in a population of cells is increased by at least ten-fold.

Apoptosis refers to the process of programmed cell death. Apoptosis guides cell selection and regulation of cell population in the developing organism. In a mature organism, apoptosis additionally functions to rid the body of damaged or mutated cells. Cancerous cells which exhibit abnormal proliferation are thought to lack the ability to undergo appropriate apoptotic cell death. The process of apoptosis differs from simple necrosis, which is a non-programmed form of cell death in response to injury. In some embodiments, the invention provides methods for increasing the number of cells in a cell population in, or undergoing, apoptosis, while not increasing the number of cells in, or undergoing, necrosis. Apoptosis can be measured by standard assays that are well known to those of skill in the art. Such assays include analysis of DNA ladder formation, TDT-mediated dUTP-biotin, nick end labeling (TUNEL), cell morphology, caspase-3 activation, etc.

When necessary, the EGFR inhibitor and the IL-6 inhibitor as described above can be administered in conjunction with an additional anti-cancer therapy. In one example, these inhibitors are administered in combination with one or more additional therapeutic agents, simultaneously or sequentially. When the additional therapeutic agents are administered simultaneously with the EGFR/IL-6 inhibitors, they can be administered in the same or separate formulations. Alternatively, the one or more additional therapeutic agents can be administered sequentially with one another and with the EGFR/IL-6 inhibitors. The separation in time between the administration of these agents may be a matter of minutes or it may be longer, which is within the knowledge of a skilled artisan. In another example, the EGFR inhibitor/IL-6 inhibitor treatment is performed together with anti-cancer radiation and/or surgical procedures.

The one or more additional therapeutic agents include, but are not limited to, anti-proliferative compounds, anti-neoplastic compounds, anti-cancer supplementary potentiating agents and radioactive agents. One of ordinary skill in the art is familiar with a variety of anti-cancer agents, or can find those agents in the routine art, which are used in the medical arts to treat cancer.

In addition, the one or more additional therapeutic agents are an anti-inflammatory compounds. As used herein, the term "anti-inflammatory compound" refers to an agent effective in suppressing inflammation. Via suppression of local inflammation, an anti-inflammatory compound can reduce the level of IL-6 in a tumor microenvironment. Anti-inflammatories include, but are not limited to non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade, Centocor, Inc., Malvern, Pa.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

Further, the one or more additional therapeutic agents are immunosuppressants. As used herein, the term "immunosuppressant" refers to an agent effective in suppressing an immune response. Immunosuppressants include, but are not limited to cyclosporin A (CSA) and FK506; monoclonal antibodies such as anti-tumor necrosis factor α (anti-TNFα), anti-CD54, anti-CD11, anti-CD11a, and anti-IL-1; and, other soluble receptors such as rTNFα. and rIL-1.

The EGFR inhibitor and the IL-6 inhibitor can be mixed with a pharmarceutically acceptable carrier, either taken alone or in combination with the one or more additional therapeutic agents described above, to form pharmaceutical compositions. A pharmaceutically acceptable carrier is compatible with the active ingredient of the composition (and preferably, capable of stabilizing it). Actual dosage levels of active ingredients in the pharmaceutical compositions of the invention can be varied to obtain an amount of the active inhibitor that is effective to achieve the desired therapeutic response for a particular patient, inhibitor, and mode of administration. The selected dosage level depends upon the activity of the particular inhibitor, the route of administration, the severity of the condition being treated, the condition, and prior medical history of the patient being treated. However, it is within the skill of one in the art to start doses of the inhibitor at levels lower than required to achieve the desired therapeutic effort and to gradually increase the dosage until the desired effect is achieved.

The pharmaceutical compositions described herein can be administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, brain, or in the cornea.

The inhibitors and pharmaceutical compositions described herein also can be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to a agent of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33, et seq.

Dosage forms for topical administration of the inhibitors and pharmaceutical compositions described herein include powders, sprays, ointments, and inhalants as described herein. The active agent is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Pharmaceutical compositions for parenteral injection comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

Compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the inhibitor(s), it is desirable to slow the absorption of the drug from subcutaneous or intramuscular injection. This result can be accomplished by the use of a liquid suspension of crystalline or amorphous materials with poor water solubility. The rate of absorption of the inhibitor(s) then depends upon its rate of dissolution which, in turn, may depend upon crystal size and crystalline form. Alternatively, delayed absorption of a parenterally administered inhibitor(s) is accomplished by dissolving or suspending the inhibitor(s) in an oil vehicle.

Injectable depot forms are made by forming microencapsule matrices of the inhibitor(s) in biodegradable polymers such a polylactide-polyglycolide. Depending upon the ratio of inhibitor(s) to polymer and the nature of the particular polymer employed, the rate of inhibitor(s) release can be controlled. Examples of other biodegradable polymers include poly(orthoesters) and poly(anhydrides). Depot injectable formulations also are prepared by entrapping the inhibitor(s) in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

Also described here are methods for oral administration of the pharmaceutical compositions described herein. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes the inhibitor(s) and inert ingredients which protect against degradation in the stomach and which permit release of the biologically active material in the intestine.

In such solid dosage forms, the inhibitor(s) is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In a most preferred embodiment, the excipient or carrier increases uptake of the inhibitor(s), overall stability of the inhibitor(s) and/or circulation time of the inhibitor(s) in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropylmethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions which can be used include polymeric substances and waxes.

The inhibitor(s) also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the inhibitor(s), the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage. Oral composition can also be administered by oral gavage.

Suspensions, in addition to the inhibitor(s), can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the EGFR inhibitors and IL-6 inhibitors. The inhibitors are delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989)($\alpha$1-antitrypsin); Smith et al., J. Clin. Invest. 84:1145-1146 (1989) ($\alpha$1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of the inhibitor(s) described herein. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise an agent of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the agent suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the inhibitor and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the inhibitor(s) and compositions of the invention also are contemplated. Nasal delivery allows the passage of the inhibitor(s) or composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the EGFR inhibitors and IL-6 inhibitors with suitable nonirritating excipients or carriers, such as cocoa butter, polyethylene glycol, or suppository wax, which are solid at room temperature, but liquid at body temperature, and therefore melt in the rectum or vaginal cavity and release the active agent.

In order to facilitate delivery of inhibitor(s) across cell and/or nuclear membranes, compositions of relatively high hydrophobicity are preferred. Inhibitor(s) can be modified in a manner which increases hydrophobicity, or the agents can be encapsulated in hydrophobic carriers or solutions which result in increased hydrophobicity.

In one aspect, the invention provides kits comprising a pharmaceutical composition comprising a therapeutically effective amount of one or more EGFR inhibitors and a therapeutically effective amount of one or more IL-6 inhibitors and instructions for administration of the pharmaceutical composition. In some aspects of the invention, the kit can include a pharmaceutical preparation vial, a pharmaceutical preparation diluent vial, and the EGFR inhibitors and IL-6 inhibitors. The diluent vial contains a diluent such as physiological saline for diluting what could be a concentrated solution or lyophilized powder of the agent of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the EGFR inhibitors and IL-6 inhibitors. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

Materials and Methods:

Cell Culture and Reagents

The mutant EGFR expressing cell lines NCI-H1650, HCC827 and HCC4006 were obtained from the American Type Culture Collection (Manassas, Va.). The PC9 cell line was obtained from Dr. Jeff Engelman (MGH, Boston). All the cell lines were maintained in RPMI-1640 GlutaMAX in the presence of 5% fetal bovine serum (FBS), 50 U/ml penicillin/streptomycin and 1 mM sodium pyruvate. Erlotinib hydrochloride was purchased from LGM Pharmaceuticals Inc. (Boca Raton, Fla.). Recombinant Interleukin-6 (rhIL6), anti-IL-6 monoclonal antibody (MAB206) and anti-IL6R (receptor) antibody (AB-227-NA) were obtained from R&D systems (Minneapolis, Minn.). Human recombinant EGF was purchased from Millipore (Billerica, Mass.). The JAK 1/2 inhibitor tetracyclic pyridone 2-tert-butyl-9-fluoro-3,6-dihydro-7H-benz[h]-imidaz[4,5-f] isoquinoline-7-one, pyridone 6 (P6) was purchased from Calbiochem (San Diego, Calif.).

Generation of Erlotinib Resistant Cells, Cell Growth Assay, and Sensitivity to Erlotinib NCI-H1650 cells were plated sub-confluently and treated for 1 month in the presence of 20 µM of erlotinib. To measure cell growth, cells were seeded in a 96 well plate. The cells were subsequently fixed at 2, 4, 6 days and the cell number was estimated using the MTT assay, following the manufacturer's protocol (Sigma, St. Louis, Mo.). Each data point represents the mean value of eight wells. Sensitivity to erlotinib was determined as follows: 1500 cells per well were seeded in 96 wells plates. After 16 hours cells were treated with indicated concentrations of erlotinib. At the 72 hours time point after seeding, 5 µl of 5 mg/ml 3-(4,5-dimethylthiazol-2-yl)-2,5-diphenyltetarzolium bromide (Sigma) was added to each well. After 2 hours of incubation at 37° C., the medium was removed and the MTT was solubilized by the addition of 50 µl of acidic isopropanol (0.1NHCL) to each well. The absorbance was determined spectrophotometrically at 570 nm. Each time point represents the average value of eight individual wells. In order to determine the effect of IL-6 on erlotinib sensitivity, cells were pretreated with IL-6 for 24 h (20 ng/mL).

Soft Agar Assay

Cells were plated in triplicate in 12-well plates at 5000 cells/well, mixed in RPMI-1640, 5% FBS and 0.35% agarose. Cells were cultured for 20 days in presence of the indicated treatment. Colonies were visualized by staining with tetrazolium salt (Schaeffer W. I., Friend K. (1976) Cancer Lett 1:259-262). The number of colonies were determined using the J-Image software (htpp://rsbweb.hih.gov/ij/) on Z-stack images (Z=1.5 mm) at 5× magnification. Each data point represents the average of 3 fields from 3 individual wells.

siRNA-Mediated Inhibition of IL-6 Expression

To target the IL-6 gene, commercially prepared Stealth RNAi siRNA (I) HSS105338, (II) HSS105339, and (III) HSS105337 were obtained from Invitrogen. Transfection of siRNAs was performed using Lipofectamine 2000 (Invitrogen) per the manufacturer's instructions. Two days after transfection, mRNA levels were determined by RT-PCR and sensitivity to erlotinib was determined as previously described. Stable knockdown efficiency was obtained even at 10 days following transfection.

Mouse Model System

The in vivo mouse experiments were performed by inoculating subcutaneously $3 \times 10^6$ NCI-H1650 cells subcutaneously into each flank of immunodeficient Nu/Nu mice in Swiss CD1 background (Charles River Breeding Laboratories, Wilmington, Mass.). After the tumors reached a volume of approximately 100 mm$^3$, mice were treated topically every 2 days with TPA (10 µL of 0.25 mg/mL solution in acetone) or with acetone for 5 days. After this treatment, erlotinib (50 mg/kg) or vehicle alone (DMSO) was delivered daily by oral gavage for 12 days. Tumor volume was monitored with a digital caliper and calculated using the following formula: (length)×(width)/2. The neutralizing antibody against IL-6 (2 mg in PBS, AB-406-NA, R&D systems) was injected intraperitoneally one day before erlotinib treatment began.

Immunohistochemistry, Immunofluorescence and Quantification

Formalin-fixed, paraffin-embedded sections (4 µm) were stained for IL-6. Sections were de-embedded and rehydrated and epitope retrieval was performed by heating the sections in 0.01 M citrate buffer at pH 6.0 in a microwave oven for 10 minutes. Endogenous peroxidase activity was blocked by treatment with 3% hydrogen peroxide in PBS for 10 minutes. After washing with PBS the blocking was performed using the Avidin/Biotin blocking kit (Vector laboratories, Cambridge, UK), Super Block (ID laboratories, London, CDN) and Mouse Block (ID laboratories, London, CDN). The sections were incubated with the primary antibody IL-6 (ab6672; Abcam, Cambridge, UK) in 1:300 dilution at 4° C. overnight. The IHC detection was done with the IDetect Super Stain System HRP (ID laboratories, London, CDN). The signal was visualized with 3-amino-9-ethylcarbazole (ID laboratories, London, CDN). Afterwards the sections were counterstained with hematoxilin.

Double immunofluorescence staining for the apoptotic and proliferating cells was performed using the TUNEL Apoptag Plus kit (Chemicon, Temecula, Calif.) according to the manufacturer's instructions and Ki67 staining (Novocastra Laboratories, Newcastle, UK) was done on the same slides. For Ki67 staining the goat-anti rabbit Alexa Flour 594 (Molecular Probes, Eugene, Oreg.) was used as secondary antibody. The counterstaining was done with DAPI.

Protein expression was measured by defining regions of interest (ROI) using automated cell acquisition and quantification software for Immunohistochemistry (Histoquest™) and immunofluorescence (Tissuequest™).

Enzyme-Linked Immunosorbent Assay

Cells were grown to approximately 80% confluency. Cells were washed with 1×PBS and fresh media was added. After 24 hours the supernatant was collected and analyzed for IL-6 using an ELISA kit (Diaclone, Canton, Mass.) following the manufacturers instruction.

Western Blot Analysis

Adherent cells were washed with 1×PBS and whole cell lysate was extracted and western blot analysis was performed as previously described (Sordella et al. Science 305, 1163-1167; 2004). Antibodies against phosphor-EGFR (Tyr1068), total Akt, phospho-Akt (Ser473), total ERK 1/2, phospho-ERK 1/2 (Thr202/tyr204), phospho-STAT3 (Tyr705), cleaved PARP and phospho-MET (Tyr1234/Tyr1235) were purchased from Cell Signaling Technology (Danvers, Mass.). Total cMET and total EGFR antibodies were purchased from Santa Cruz Biotechnology (Santa Cruz, Calif.). The antibody against total STAT3 was purchased from BD Biosciences (San Jose, Calif.).

Genomic DNA Extraction and Mutational Analysis

Genomic DNA extraction was performed as described in "Molecular Cloning" by Sambrook and Russell. KRAS exons and EGFR exons were amplified by mean of the Pfu-Ultra (Stratagene, LA Jolla, Calif.) using the following primers:

KRAS exon 2 fwd: CTTAAGCGTCGATGGAG (SEQ ID NO:1); rev: ATCCTCATCTGCTTGGGATG (SEQ ID NO:2)

KRAS exon 3 fwd: AAATAGTGCTGCTGCAACA (SEQ ID NO:3); rev: CTAGGTTTCAATCCCAGCA (SEQ ID NO:4)

EGFR exon 19 fwd: GCAATATCAGCCTTAGGTGCG-GCTC (SED ID NO:5); rev: CATAGAAAGTGAACATT-TAGGATGTG (SED IS NO:6)

EGFR exon 20 fwd: CCATGAGTACG-TATTTTGAAACTC (SED IS NO:7); rev: CATATC-CCCATGGCAAACTCTTGC (SED IS NO:8).

PCR products were purified using PrepEase® Gel Extraction Kit (USB corporation, Cleveland, Ohio) and sequenced using the following primers:

KRAS exon 2 fwd: AAGGCCTGCTGAAAATGACTG (SEQ ID NO:9); rev: CTGTATCAAAGAATGGTCCTG-CAC (SEQ ID NO:10)

KRAS exon 3 fwd: CCAGACTGTGTTTCTCCCTTCT-CAG (SEQ ID NO:11); rev: AACCCACCTATAATGGT-GAA (SEQ ID NO:12)

EGFR exon 19 fwd: CCTTAGGTGCGGCTCCACAGC (SEQ ID NO:13); rev: CATTTAGGATGTGGAGATGAGC (SEQ ID NO:14)

EGFR exon 20 fwd: GAAACTCAAGATCGCAT-TCATGC (SEQ ID NO:15); rev: GCAAACTCTTGCTATC-CCAGGAG (SEQ ID NO:16)

Real-Time and Semi-Quantitative PCR

Total cellular RNA was isolated from sub-confluent plates using TRIzol reagent (Invitrogen) and was treated with RQ1 RNase free DNase (Promega, Madison, Wis.). RNA (1 µg) was reverse transcribed using ImProm-II Reverse Transcriptase (Promega). Reactions were performed according to manufacturer's instructions. PCR reactions were performed to assess gene expression levels using the following primers:

IL-6 (fwd: TAGCCGCCCCACACAGACAG (SEQ ID NO:17); rev: GGCTGGCATTTGTGGTTGGG (SEQ IS NO:18)), LIF (fwd: TGCCAATGCCCTCTTTATTC (SEQ IS NO:19), rev: GTTGACAGCCCAGCTTCTTC (SEQ ID NO:20)), OSM (fwd: GCACTCCTGTTTCCAAGCAT (SEQ ID NO:21), rev: CTGCTCTAAGTCGGCCAGTC (SEQ ID NO:22)), CSF-1 (fwd: CACCATGCGCTTCAGAGATA (SEQ ID NO:23), rev: GCTGATGAGGGGAGACAGAG (SEQ ID NO:24)), CNtf (fwd: GGACCTCTGTAGCCGCTCTA (SEQ ID NO:25), rev: AGCTCCTGCAGCACCTTTAG (SEQ ID NO:26)), EGF (fwd: GATCTCGATGGTGTGGGAGT (SEQ ID NO:27), rev: ATCTTCTGCCTTGGGTTGTG (SEQ ID NO:28)), IL-1A (fwd: TGTAAGCTATGGCCCACTCC (SEQ IS NO:29), rev: AGCAGCCGTGAGGTACTGAT (SEQ ID NO:30)), IL-11 (fwd: CTGAGCCTGTGGCCAGATA (SEQ ID NO:31), rev: CCGCAGGTAGGACAGTAGGT (SEQ ID NO:32)), ACTIN (fwd: GCATGGGTCAGAAGGATTC (SEQ ID NO:33), rev: CATCTCTTGCTCGAAGTCC (SEQ ID NO:34)).

Generation of an In Vitro Cell-Based System to Study Erlotinib Resistance

The broncho-alveolar cancer cell line NCI-H1650 that harbors an oncogenic deletion within the EGFR (delE746-A750) typically displays an IC50 to either gefitinib or erlotinib treatment of approximately 5 µM. By culturing this cell line in the presence of a constant high concentration of erlotinib drug, an isolated cell line capable of growing in the presence of up to 30 µM of erlotinib was generated. The NCI-H1650 M3 cells were identified as having decreased erlotinib sensitivity without having acquired any of the previously described molecular mechanisms of erlotinib/gefitinib acquired resistance (i.e., EGFR T790M and c-MET amplification), indicating that this was a novel mechanism of acquired resistance.

Statistical Analysis

Data are presented as mean+/− standard deviation. Two-tailed Student's t-test was used to assess statistical significance between observed differences. Bonferroni correction of the alpha level was used when multiple comparisons were made. P values <0.05 were considered significant. All statistical analysis was performed using Intercooled Stata, version 8 statistical software.

Results:

(i) EGFR-independent STAT 3 Phosphorylation is Increased in Erlotinib Resistant Cells Erlotinib resistant cells (NCI-H1650 M3) were generated by growing parental NCI-H1650 cells (sensitive to erlotinib) in erlotinib at high concentrations. The parental and resistant cells were grown in the presence of erlotinib at various concentrations (0.3125, 0.625, 1.25, 2.5, 5, and 10 µM) and the numbers of viable cells were measured 72 hours after the treatment. As shown in FIG. 1, Panel A, the cell viability of NCI-H1650 M3 cells was much higher than that of the parental cells, particularly at high erlotinib concentrations.

The capacity of erlotinib to suppress components of the EGFR-axis in parental cells (sensitive to erlobinib) and erlotinib-resistant cells (NCI-H1650 M3) was investigated using western blot analysis. Briefly, parental and resistant cells were exposed to increasing concentrations of erlotinib (0.01, 0.1, 1, and 10 µM) for 3 hours and cell extracts prepared from these cells were immunoblotted to detect levels of expression and phosphorylation of Tubulin, STAT3, P-STAT3, AKT, P-AKT, EGFR, and P-EGFR. The erlotinib-resistant cells maintained high STAT3 phosphorylation levels even in the presence of high concentration of erlotinib (i.e., 10 µM) while phosphorylated STAT3 was undetectable in parental cells at high erlotinib concentrations. There was a comparable inhibition of EGFR phosphorylation levels upon erlotinib treatment and aberrant activation of a selective anti-apoptotic signalling pathway downstream EGFR was responsible for the acquired resistance of the NCI-H1650 M3 cell line.

STAT3 and AKT activation had already been shown to be required for cell survival in cells harboring mutant EGFR (See e.g., Akca et al., Lung Cancer 54, 25-33, 2006). Immunoblot analysis indicated that while levels of phosphorylation of AKT were similarly inhibited in the two cell lines, STAT3 phosphorylation levels were elevated in the resistant cells relative to those in parental cells even in the presence of high concentrations of erlotinib, implying an activation of STAT3 in erlotinib-resistance cells independently of EGFR.

Furthermore, as shown in FIG. 1, Panel B, the substantial decrease in the cleavage of PARP upon erlotinib treatment of the NCI-H1650 M3 erlotinib-resistant cells compared to the parental-sensitive cells indeed indicated that a decrease in apoptosis accounts for the observed erlotinib resistance. In this study, parental and resistant cells were exposed to erlotinib (10 µM concentration) for 24 hours and their cell extracts were analyzed by immunoblot for cleaved PARP.

(ii) Interleukin-6 is the Main Factor Responsible for the EGFR-Independent Stat3 Phosphorylation in the Erlotinib Resistant Cells Cells were starved for 30 minutes, 2, 8, 16, or 32 hours and cell extracts were immunoblotted for phospho-STAT3 and STAT3. The results show that serum deprivation decreased the amount of STAT3 phosphorylation, but after 32 hours of starvation levels had returned to those initially observed. This indicates that levels of STAT3 phosphorylation depend upon growth conditions. Thus, increased EGFR-independent STAT3 phosphorylation observed in the erlotinib-resistant cells is explained by the secretion of an autocrine factor rather than by mutations in kinases known to induce STAT3 phosphorylation such as, for example, Jak1 or Jak2.

To determine protein factors that might responsible for the activation of STAT3 in NCI-H1650 M3 cells, the cells were starved for 30 minutes and then stimulated with media collected from the starved-cells for 1 hour or 16 hours. Cell extracts were immunoblotted for phospho-STAT3 and total STAT3. As a control the conditioned medium was boiled prior to addition to the cells. Serum-deprived erlotinib-resistant cells were stimulated with conditioned medium obtained from the NCI-H1650 M3 cells. Western blot analysis indicated that phosphorylation of STAT3 was induced in serum-starved cells within 5 minutes of treatment. Because these changes were abrogated by heat inactivation of the conditioned medium, it followed that a secreted protein had to be responsible for the activation of STAT3 observed in the resistant cells.

The mRNA levels of various secreted proteins, including HGF, EGF, LIF, CNTF, IL-1A, IL-11, OSM and IL-6 (which are known to increase STAT3 phosphorylation), were examined by RT-PCR, the results normalized against beta-actin mRNA levels. No substantial levels of HGF were detected in either the parental-sensitive cells or in the resistant cells. Among these protein factors, a substantial increase in IL-6 mRNA levels was found in the resistant cells as compared to parental cells. This increase in IL-6 mRNA expression correlated with augmented levels of the protein secretion as determined by enzyme-linked immunosorbent assay (ELISA). See FIG. 2, Panel A; levels of IL-6 were measured by ELISA with each point representing the average of four data points. Results from this study also show that IL-6 levels, determined by an ELISA assay, in the media of the NCI-H1650 M3 cells did not change in the presence of erlotinib (10 µM).

To determine whether IL-6 was the autocrine factor responsible for promoting STAT3 phosphorylation in the erlotinib-resistant cells, the expression of IL-6 was inhibited using siRNA technology. Briefly, NCI-H 1650 M3 cells were transfected with siRNA targeting IL-6 (siRNA I and II) or a non-specific siRNA (siRNA III) using Lipofectamine 2000 at a final concentration of 30 nM siRNA. After 6 days cell extracts were analyzed by immunoblotting for phospho-STAT3, STAT3 and tubulin. Upon transfection of siRNA duplexes selectively targeting the IL-6 transcript, STAT3 phosphorylation in the resistant cells was drastically reduced. Thus, an increased secretion of IL-6 was responsible for the observed STAT3 phosphorylation. To confirm this conclusion, NCI-H1650 M3 cells were treated with 1 µg/ml IL-6 neutralizing antibody, 10 µg/ml IL-6 receptor antibody (anti-gp130), or 2 µM pan-JAK inhibitor P6 for 2 days. Cell extracts were analyzed by immunoblot for phospho-STAT3 and total STAT3. The results thus obtained show that all of the IL-6 neutralizing antibodies, the anti-IL-6 receptor antibody and the pan-JAK inhibitor decreased STAT3 phosphorylation levels. In sum, inhibition of the IL-6 axis decreased levels of phosphorylation of STAT3.

Figure 2:
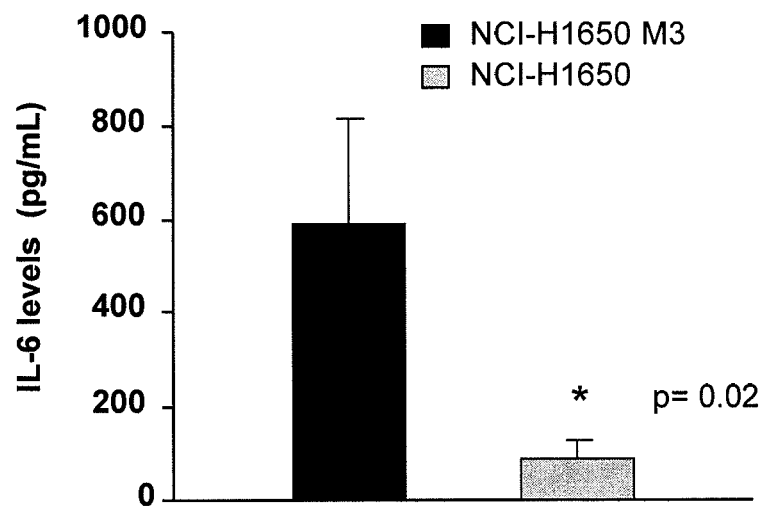
FIG. 2 is a diagram showing that Interleukin-6 is associated with erlotinib resistance of cancer cells. Panel A: a bar graph showing levels of IL-6 in NCI-H1650 and NCI-H1650 M3 cells. The dark bar represents NCI-H1650 M3 cells and the light bar represents in NCI-H1650 cells. Panel B: a bar graph showing blockage of IL-6 signaling via IL-6 targeting siRNAs increased the cell sensitivity to erlotinib. The dark bar represents untreated cells, the grey bar represents cells treated with a non-specific siRNA (siRNA III), and the light bar represents cells treated with IL-6-specific siRNAs (siRNA I and siRNA II). Panel C: a bar graph showing the percentage of viable cells (relative to control cells) in the presence of an IL-6 neutralizing antibody (10 µg/ml) or of the pan-JAK inhibitor P6 (2 µM). The dark bar represents untreated cells, the grey bar represents cells treated with an IL-6 neutralizing antibody, and the light bar represents cells treated with pan-JAK inhibitor P6.
Figure 2:
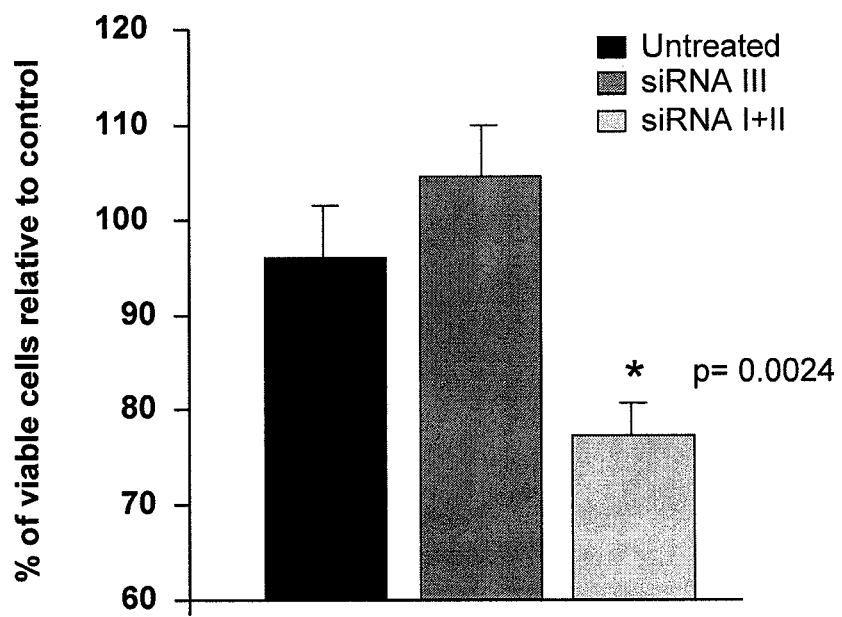
Figure 2:
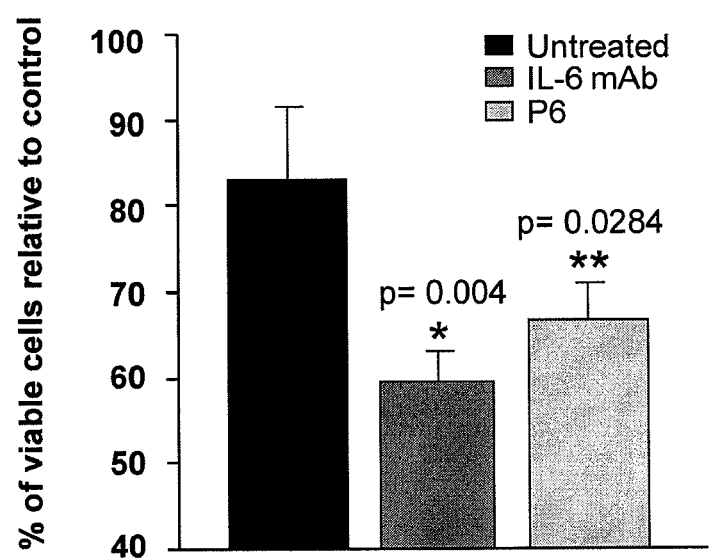

To explore the association between IL-6 signaling and cell sensitivity to erlotinib, resistant cells were transfected with the siRNA mentioned above. Two days later, the cells were seeded and treated for 72 hours with erlotinib at a concentration of 5 µM. Viability was measured by MTT assay relative to untreated cells, with each data point showing the average of four replicates. As shown in FIG. 2, Panel B, IL-6-targeting siRNAs I and II, but not non-specific siRNA III, successfully restored cell sensitivity to erlonitib. Similar results were observed in cells treated with anti-IL-6 antibody. See FIG. 2, Panel C.

(iii) IL-6 is Required and Sufficient to Modify Sensitivity of Cells to Erlotinib Treatment The viability of the NCI-H1650 M3 cells upon inhibition of IL-6 mediated signalling was determined to evaluate if EGFR-independent up-regulation of IL-6/gp130/STAT3 axis in NCI-H1650 M3 cells was responsible for erlotinib resistance. As illustrated in FIG. 2, Panels B and C, reduction of the level of IL-6 by siRNA, as well as inhibition of the IL-6 axis by means of an IL-6 neutralizing antibody or a JAK1/2 inhibitor, significantly decreased the NCI-H1650 M3 cells viability upon erlotinib treatment. Thus the increased autocrine production of IL-6 in the erlotinib resistant cells is sufficient to modify sensitivity of the cells to erlotinib treatment.

Since both the parental-sensitive cells as well as the resistant cells express similar level of IL-6 receptor, it followed that stimulation of cells with IL-6, in addition of being required for erlotinib resistance in the NCI-H1650 M3 cells, should also be sufficient to decrease cell sensitivity to erlotinib treatment in cells expressing mutant EGFR. Immunblot analysis of cell extracts from NCI-H160 cells, NCI-H1650 M3 cells, and NCI-H1993 cells showed that the latter harbor an amplification of c-MET and as such are used as a control for c-MET over-expression and c-MET over-activation.

The effect of IL-6 on the viability of multiple NSCLC cell lines (i.e., NCI-H1650, HCC 827, PC9 and HCC4006) expressing mutant EGFR. These cell lines, despite all harboring somatic activating EGFR mutations, display different erlotinib sensitivity with half maximal inhibitory concentrations (IC50) ranging from 5 µM in the case of the NCI-H1650 to 0.001 µM in the case of the HCC827 (Gandhi et al., PLoS One 4, e4576, 2009).

Figure 3:
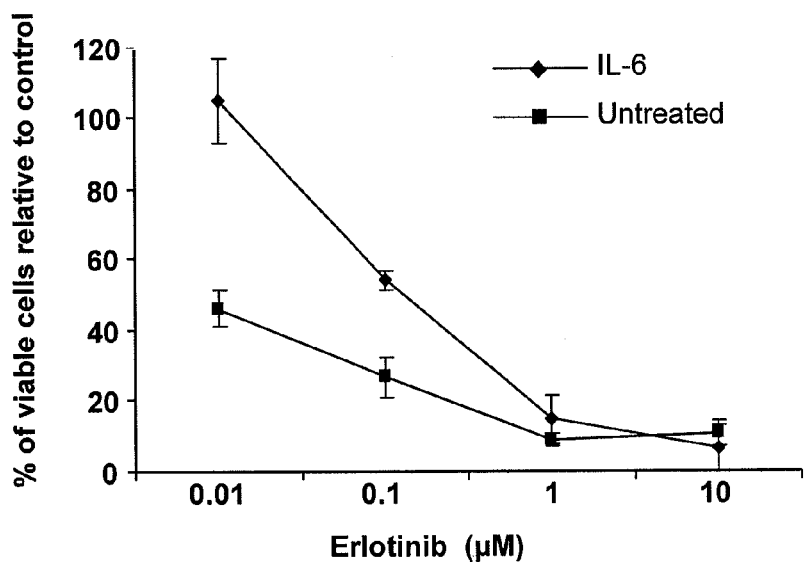
FIG. 3 is a diagram showing that IL-6 modifies sensitivity of cells to erlotinib treatment. Panel A: a chart showing viability of PC9 cells (relative to control cells) in the presence of 10 ng/mL IL-6 and erlotinib at various concentrations. Panel B: a bar graph showing viability of PC9, HCC827 and HCC4006 cells in the presence of 0.01 mM erlotinib with or without IL-6 treatment. Panel C: a bar graph showing the long-term effects of IL-6 on NCI-H1650 cells treated with erlotinib (10 mM) or DMSO (0.1%) in the presence of absence of IL-6 (10 ng/ml). Panel D: a bar graph showing restoration of cell sensitivity to erlotinib by JAK1/2 inhibitor P6 in the presence of IL-6. Panel E: a photo showing levels of apoptosis (indicated by the levels of CL-PARP) in cells treated with erlotinib in the presence or absence of IL-6.
Figure 3:
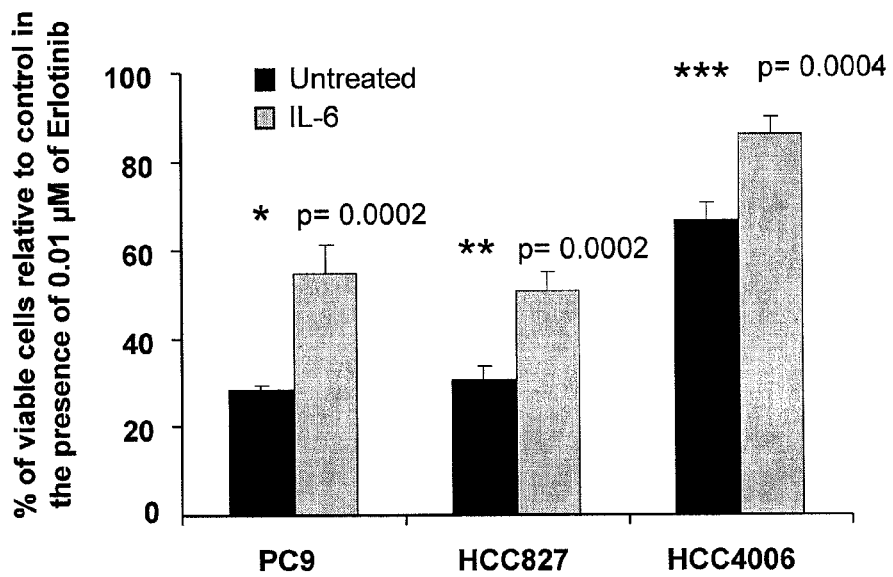
Figure 3:
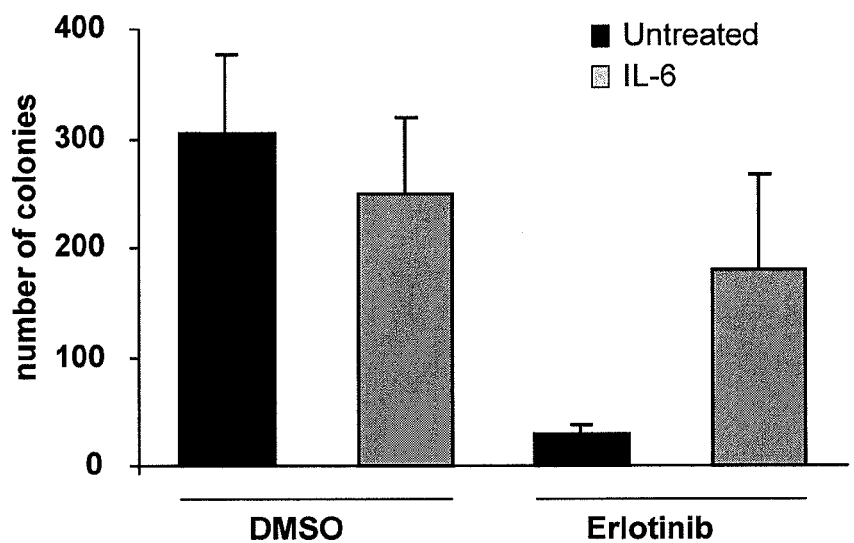
Figure 3:
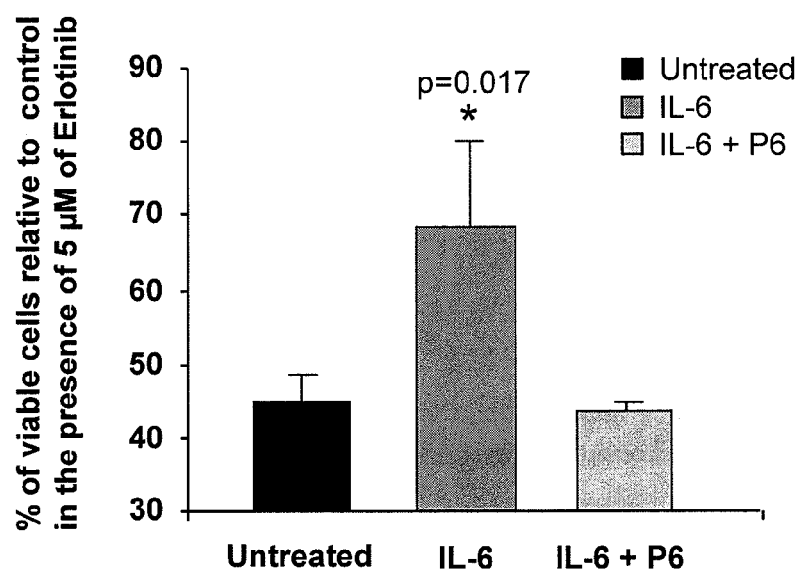
Figure 3:
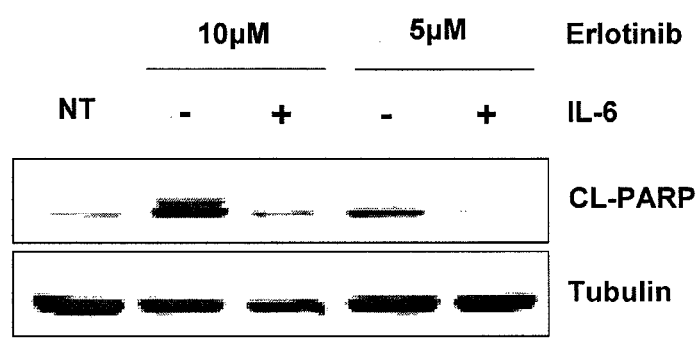

PC9 cells, harboring an EGFR oncogenic mutation, were grown in the presence of 10 ng/ml IL-6 for 24 hours and then treated with erlotinib at various concentrations. After 72 hours, the viability of cells was determined by MTT assay, viability shown relative to untreated cells. As shown in FIG. 3, Panel A, IL-6 increased PC9 cell resistance to erlotinib. Similar results were observed in PC9, HCC827, and HCC4006 cells, all carrying EGFR oncogenic mutations, at 0.011 µM erlotinib. See FIG. 3, Panel B. Thus, providing an exogenous source of IL-6 can reduce the dependency of NSCLS on mutant EGFR.

A soft agar assay, as described above, was performed to demonstrate long-term effect of IL-6 on cell sensitivity to erlotinib. NCI-H1650 cells were plated in soft agar in the presence of DMSO (untreated), or erlotinib (10 mM) with or without IL-6 (10 ng/ML). The numbers of cell colonies were countered after a suitable period of time. The number of colonies were determined using the J-image software on Z-stack images (Z=1.5.mm) at 5× magnification. The results indicate that IL-6 significantly increased cell resistance to erlotinib. See FIG. 3, Panel C (each point represents the average of 3 fields from individual wells). Similar results were obtained in a 2-day cell culture assay. When cells were pre-treated with IL-6 (10 ng/ml) and P6 (2 μM), and then treated with erlotinib (5 μM), their viability 72 hours after the erlotinib treatment was similar to control cells, indicating that IL-6 induced cell resistance to erlotinib was decreased by P6. See FIG. 3, Panel D (each bar representing the average of 4 replicates). In other words, P6 JAK1/2 inhibitor restored the cell sensitivity to erlotinib even in the presence of IL-6.

Notably, IL-6 treatment did not affect the cells proliferation rates but rather decreased their apoptotic response. No substantial changes in cell proliferation were detected upon stimulation with IL-6 (10 ng/ml). On the other hand, deceased apoptosis was observed in erlonitib-treated cells in the presence of IL-6. Resistant cells were grown in the presence or absence of IL-6 for 24 hours and then treated with erlotinib at the indicated concentrations. Cells not treated with the drug were used as a control. Cell extracts obtained after 72 hours were analyzed by immunoblotting for cleaved PARP(CL-PARP), an indicator of apoptosis status. The results indicate that the level of CL-PARP in erlotinib-treated cells was significantly increased as compared to control cells and IL-6 decreased CL-PARP levels in the drug treated cells. See FIG. 3, Panel E. This indicates that the decreased sensitivity observed in cells treated with IL-6 is due to a diminished apoptotic response.

The effect of IL-6 treatment was due to the activation of the gp130-STAT3 axis and not due to a decreased bioavailability of erlotinib, as confirmed by the activation of some of the components of the EGFR signalling pathway in cells treated with erlotinib. Cells were grown in the presence or absence of IL-6 and then treated for 4 hours with erlotinib. Cell extracts were analyzed by immunoblotting with antibodies specific to Tubulin, AKT, P-AKT, STAT3, and P-STAT3. Whereas IL-6 treatment did not have any effect on erlotinib-mediated inhibition of AKT activation, it did instead impaired inhibition of STAT3 phosphorylation. Thus, the action of IL-6, through the activation of gp130/JAK pathway, is sufficient to decrease the cells sensitivity to erlotinib.

(iv) Inflammation Induces an Increase in IL-6 Expression that Triggers Erlotinib Resistance IL-6 is a pleiotropic cytokine that exerts important biological functions in a wide variety of systems and processes (e.g., inflammation, acute-phase reaction, nervous and endocrine systems, bone metabolism, hematopoiesis). Thus, the secretion of IL-6 by the tumor micro-environment during the course of inflammation could likely impair cell sensitivity to erlotinib which can explain the high degree of heterogeneity in the response to erlotinib treatment of NSCLC tumors harboring mutant EGFR. Cutaneous inflammation and secretion of IL-6 by topic treatment of the mouse epidermis with low dose of 12-O-tetradecanoyl-phorbol-13-acetate (TPA) every other day was induced in a Nu/nu mouse model (Vasunia et al. Carcinogenesis 1994, 15: 653). Acetone was used as a vehicle control. The Nu/nu mice were subsequently injected in the flank with NSCLC expressing mutant EGFR. When the tumors reached a volume of approximately 100 $mm^3$ (typically three weeks after tumor cell inoculation), the mice epidermis were topically treated with TPA for 5 days and subsequently treated with erlotinib for 9 days at dosage equivalent to dosed used in patients.

Figure 4:
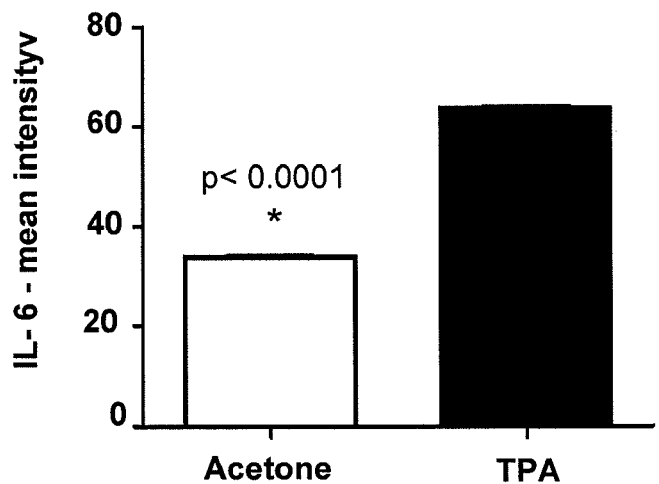
FIG. 4 is a diagram showing that inflammation induces an augmented IL-6 expression, resulting in decreased tumor sensitivity to erlotinib. Panel A: a bar graph showing the effect of TPA or acetone (a vehicle control) on IL-6 intensity in mice bearing tumor xenografts induced by NCI-1650 cells. Panel B: a bar graph showing that TPA treatment decreases the tumor's response to erlonitib. Panel C: a bar graph showing levels of tumor antigen Ki67 in tumor xenografts of TPA or acetone-treated mice. Panel D: a bar graph showing that the effect of TPA is due to decreased apoptosis in tumor matter. Panel E: a bar graph showing the effect of an anti-IL-6 antibody on tumor burden in mice treated with erlotinib.
Figure 4:
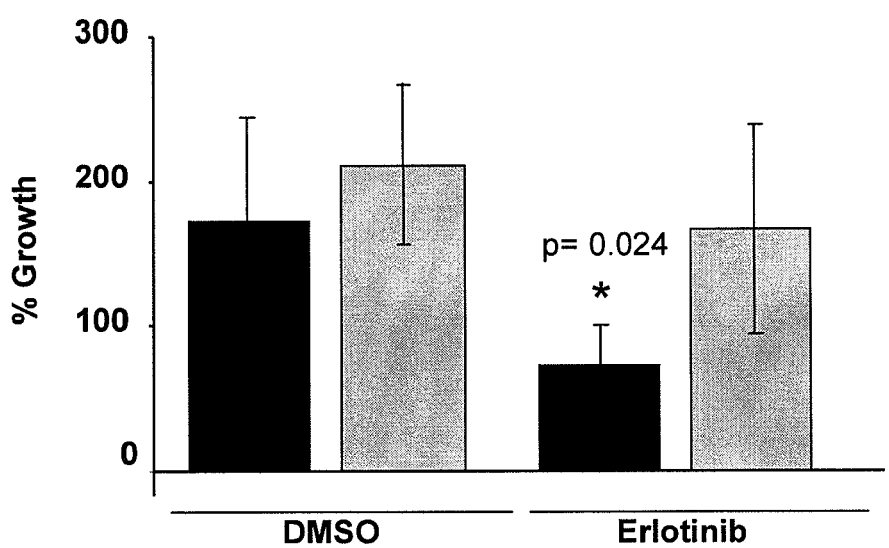
Figure 4:
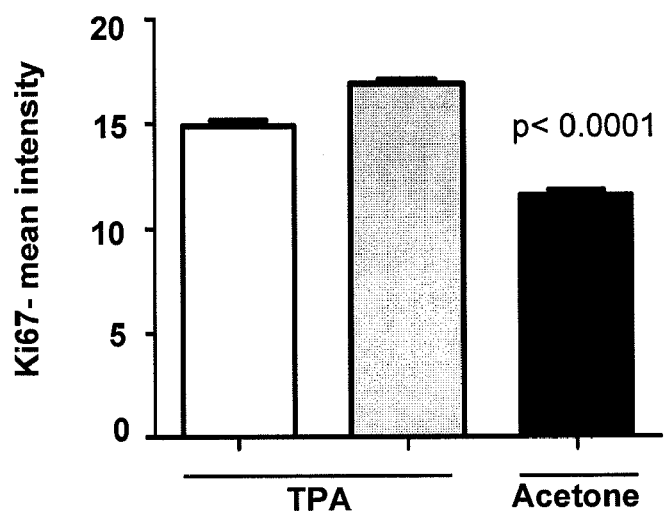
Figure 4:
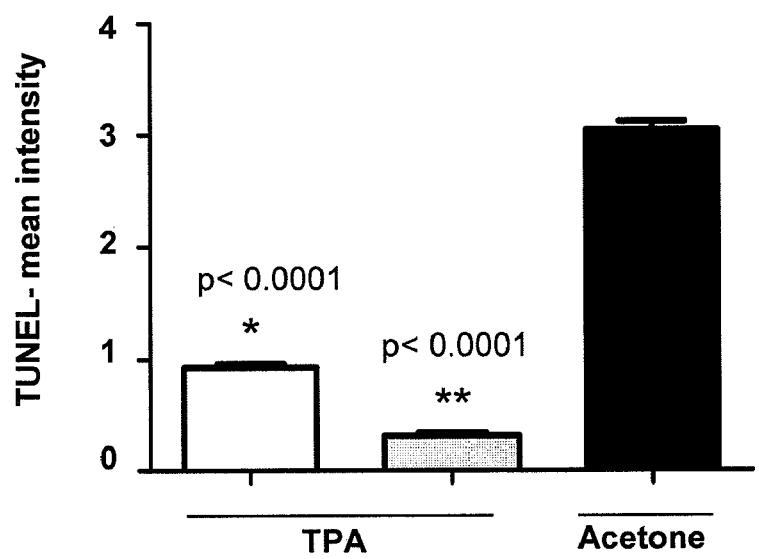
Figure 4:
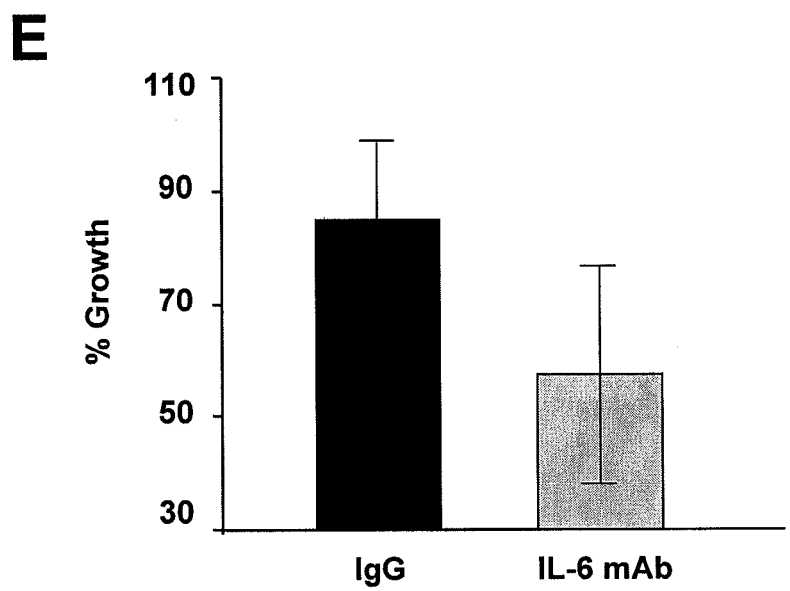

Immunostaining of tumor sections using an anti-IL-6 antibody confirmed that TPA was able to augment IL-6 expression in the tumors. For example, formalin-fixed, paraffin-embedded sections (4 μm) were stained for IL-6 and counterstained with hematoxilin.B, for ki76 in purple, tunnel assay in green, and counter-staining with DAPI in blue. The result indicates that the levels of IL-6 were much higher in TPA-treated mice than in acetone-treated mice. The levels of IL-6 in tumor matters were further measured by defining regions of interest (ROI) using automated cell acquisition and quantification software for immunohistochemistry (Histoquest™) or quantification software for immunofluorescence (Tissuequest™). As shown in FIG. 4, Panel A, the IL-6 mean intensity in TPA-treated mice was much higher than that in acetone-treated mice. By comparing the tumor burdens of mice under treatments of erlonitib or DMSO, it was observed that TPA treatment dramatically reduced the tumor response to erlotinib treatment. See FIG. 4, Panel B. The tumor burden, indicated by the Ki67 mean intensities of three representative tumors, of mice treated with TPA or acetone is shown in FIG. 4, Panel C. A TUNEL assay (which measures apoptosis) showed that the effect of IL-6 in vivo was mainly due to a decrease in apoptosis rather than an increase in cell proliferation. See FIG. 4, Panel D.

Figure 5:
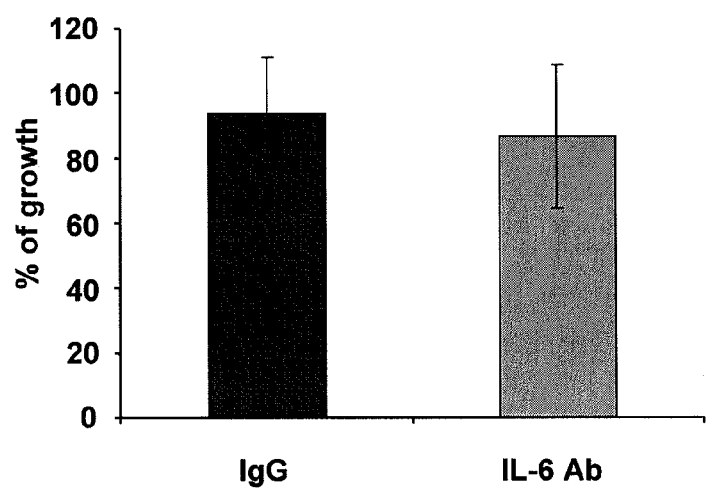
FIG. 5 is a bar graph representing the tumor burden of four tumors 8 days after erlotinib treatment in mice injected intraperitoneally with mouse IL-6 neutralizing antibody (0.08 mg/gr) or with a control IgG (0.08 mg/gr).

To determine whether an increased IL-6 produced by the tumor-microenvironment upon TPA treatment was responsible for the diminished erlotinib response, IL-6 availability was decreased by injecting the mice with an antibody that neutralizes mouse IL-6 as follows. Prior to erlotinib treatment, the tumor-bearing mice were treated with TPA as previously described and then injected intraperitoneally with mouse IL-6 neutralizing antibody (0.08 mg/gr) or a control IgG control (0.08 mg/gr). After 8 days, tumor burden was evaluated and the averages of four separate tumors were charted. Remarkably, co-treatment with a mouse IL-6 neutralizing antibody decreased the effect of TPA and increased the tumor sensitivity to erlotinib of human origin NSCLC mice. See FIG. 4, Panel E, and FIG. 5. This suggests that the effects of TPA are in part due to an increased secretion of IL-6 by the tumor micro-environment. Clearly, IL-6 is a determinant of erlotinib sensitivity in lung tumors.

OTHER EMBODIMENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

We claim:

1. A method or assessing the likelihood that a subject with Epidermal Growth Factor Receptor kinase inhibitor-resistant cancer will benefit from therapy that increases sensitivity to a Epidermal Growth Factor Receptor kinase inhibitor, the method comprising:
   (a) providing a cellular tissue sample of the subject; wherein the sample comprises non-small cell lung carcinoma cells, breast cancer cells, or pancreatic cancer cells;
   (b) determining whether the non-small cell lung carcinoma cells, breast cancer cells, or pancreatic cancer cells carry an oncogenic mutation in the Epidermal Growth Factor Receptor that is associated with Epidermal Growth Factor Receptor tyrosine kinase inhibitor resistance, and
   (c) determining the level in the sample of at least one marker selected from the group consisting of IL-6 mRNA level and IL-6 protein level, wherein presence of the oncogenic mutation and an elevated level of at least one marker in the sample as relative to a control indicates that the subject is likely to benefit from the therapy that increases sensitivity to a Epidermal Growth Factor Receptor kinase inhibitor.

2. The method of claim 1, wherein the EGFR-tyrosine kinase inhibitor is erlotinib or gefitinib.

3. The method of claim 1, wherein the oncogenic mutation in the Epidermal Growth Factor Receptor that is associated with Epidermal Growth Factor Receptor tyrosine kinase inhibitor resistance is selected from the group consisting of the variant III mutation, a KRAS mutation, a combination of L858R and T790M, and a combination of delE746-A750 and T790M.

4. The method of claim 3, wherein the oncogenic mutation in the Epidermal Growth Factor Receptor that is associated with Epidermal Growth Factor Receptor tyrosine kinase inhibitor resistance is variant III mutation.

5. The method of claim 3, wherein the oncogenic mutation in the Epidermal Growth Factor Receptor that is associated with Epidermal Growth Factor Receptor tyrosine kinase inhibitor resistance is a KRAS mutation.

6. The method of claim 3, wherein the oncogenic mutation in the Epidermal Growth Factor Receptor that is associated with Epidermal Growth Factor Receptor tyrosine kinase inhibitor resistance is a combination of L858R and T790M.

7. The method of claim 3, wherein the oncogenic mutation in the Epidermal Growth Factor Receptor that is associated with Epidermal Growth Factor Receptor tyrosine kinase inhibitor resistance is a combination of delE746-A750 and T790M.

\* \* \* \* \*

SEQUENCE LISTING

<160> NUMBER OF SEQ ID NOS: 34

<210> SEQ ID NO 1
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 1
cttaagcgtc gatggag                                                        17

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
atcctcatct gcttgggatg                                                     20

<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 3
aaatagtgct gctgcgaaca                                                     20

<210> SEQ ID NO 4
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 4
ctaggtttca atcccagca                                                      19

<210> SEQ ID NO 5
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 5
gcaatatcag ccttaggtgc ggctc                                               25

<210> SEQ ID NO 6
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 6
catagaaagt gaacatttag gatgtg                                              26

<210> SEQ ID NO 7
<211> LENGTH: 24
<212> TYPE: DNA

```
<213> ORGANISM: artificial sequence
<220> FEATURE:
<223> OTHER INFORMATION: synthetic oligonucleotide

<400> SEQUENCE: 7
ccatgagtac gtattttgaa actc                                          24

<210> SEQ ID NO 8
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 8
catatcccca tggcaaactc ttgc                                          24

<210> SEQ ID NO 9
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 9
aaggcctgct gaaaatgact g                                             21

<210> SEQ ID NO 10
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 10
ctgtatcaaa gaatggtcct gcac                                          24

<210> SEQ ID NO 11
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 11
ccagactgtg tttctcccctt ctcag                                        25

<210> SEQ ID NO 12
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 12
aacccaccta taatggtgaa                                               20

<210> SEQ ID NO 13
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 13
ccttaggtgc ggctccacag c                                             21
```

```
<210> SEQ ID NO 14
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 14
catttaggat gtggagatga gc                                              22

<210> SEQ ID NO 15
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 15
gaaactcaag atcgcattca tgc                                             23

<210> SEQ ID NO 16
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 16
gcaaactctt gctatcccag gag                                             23

<210> SEQ ID NO 17
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 17
tagccgcccc acacagacag                                                 20

<210> SEQ ID NO 18
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 18
ggctggcatt tgtggttggg                                                 20

<210> SEQ ID NO 19
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 19
tgccaatgcc ctctttattc                                                 20

<210> SEQ ID NO 20
<211> LENGTH: 20
<212> TYPE: DNA
<213> ORGANISM: artificial sequence
<220> FEATURE:
<223> OTHER INFORMATION: synthetic oligonucleotide
```

```
<400> SEQUENCE: 20
gttgacagcc cagcttcttc                                              20

<210> SEQ ID NO 21
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 21
gcactcctgt ttccaagcat                                              20

<210> SEQ ID NO 22
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 22
ctgctctaag tcggccagtc                                              20

<210> SEQ ID NO 23
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 23
caccatgcgc ttcagagata                                              20

<210> SEQ ID NO 24
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 24
gctgatgagg ggagacagag                                              20

<210> SEQ ID NO 25
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 25
ggacctctgt agccgctcta                                              20

<210> SEQ ID NO 26
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 26
agctcctgca gcacctttag                                              20

<210> SEQ ID NO 27
<211> LENGTH: 20
<212> TYPE: DNA
```

```
<213> ORGANISM: artificial sequence
<220> FEATURE:
<223> OTHER INFORMATION: synthetic oligonucleotide

<400> SEQUENCE: 27
gatctcgatg gtgtgggagt                                              20

<210> SEQ ID NO 28
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 28
atcttctgcc ttgggttgtg                                              20

<210> SEQ ID NO 29
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 29
tgtaagctat ggcccactcc                                              20

<210> SEQ ID NO 30
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 30
agcagccgtg aggtactgat                                              20

<210> SEQ ID NO 31
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 31
ctgagcctgt ggccagata                                               19

<210> SEQ ID NO 32
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 32
ccgcaggtag gacagtaggt                                              20

<210> SEQ ID NO 33
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 33
gcatgggtca gaaggattc                                               19
```

```
<210> SEQ ID NO 34
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 34
catctcttgc tcgaagtcc                                                    19
```